(12) United States Patent
Sivakumar et al.

(10) Patent No.: US 8,222,374 B2
(45) Date of Patent: Jul. 17, 2012

(54) IL-21 ANTAGONISTS

(75) Inventors: Pallavur V. Sivakumar, Seattle, WA (US); Stephen R. Jaspers, Edmonds, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/037,585

(22) Filed: Mar. 1, 2011

(65) Prior Publication Data

US 2011/0172399 A1     Jul. 14, 2011

Related U.S. Application Data

(60) Continuation of application No. 12/179,003, filed on Jul. 24, 2008, now Pat. No. 7,923,539, which is a division of application No. 11/563,928, filed on Nov. 28, 2006, now abandoned.

(60) Provisional application No. 60/740,154, filed on Nov. 28, 2005.

(51) Int. Cl.
*A61K 39/395*     (2006.01)
*C07K 16/24*      (2006.01)
*C12P 21/08*      (2006.01)

(52) U.S. Cl. ............... 530/388.15; 530/350; 530/387.3; 530/388.1; 530/809; 424/133.1; 424/70.21

(58) Field of Classification Search .................. None
See application file for complete search history.

(56) References Cited

U.S. PATENT DOCUMENTS

| | | | |
|---|---|---|---|
| 6,057,128 A | 5/2000 | Donaldson et al. |
| 6,307,024 B1 | 10/2001 | Novak et al. |
| 6,605,272 B2 | 8/2003 | Novak et al. |
| 6,682,736 B1 | 1/2004 | Hanson et al. |
| 6,686,178 B2 | 2/2004 | Novak et al. |
| 6,929,932 B2 | 8/2005 | Presnell et al. |
| 7,473,765 B2 | 1/2009 | Novak et al. |
| 7,491,800 B2 | 2/2009 | Novak et al. |
| RE41,129 E | 2/2010 | Novak et al. |
| 7,923,539 B2 | 4/2011 | Sivakumar et al. |
| 2003/0108549 A1 | 6/2003 | Carter et al. |
| 2004/0016010 A1 | 1/2004 | Kasaian et al. |
| 2004/0136954 A1 | 7/2004 | Grusby et al. |
| 2004/0260065 A1 | 12/2004 | Novak et al. |
| 2005/0193434 A1 | 9/2005 | Leonard et al. |
| 2006/0024268 A1 | 2/2006 | Kasaian et al. |
| 2006/0039902 A1 | 2/2006 | Young et al. |
| 2006/0159655 A1 | 7/2006 | Collins et al. |
| 2007/0014800 A1 | 1/2007 | Novak et al. |
| 2007/0041974 A1 | 2/2007 | Novak et al. |
| 2007/0048259 A1 | 3/2007 | Novak et al. |
| 2007/0048260 A1 | 3/2007 | Novak et al. |
| 2007/0048845 A1 | 3/2007 | Novak et al. |
| 2007/0049529 A1 | 3/2007 | Novak et al. |
| 2007/0054320 A1 | 3/2007 | Novak et al. |
| 2007/0059825 A1 | 3/2007 | Novak et al. |
| 2007/0066807 A1 | 3/2007 | Novak et al. |
| 2007/0066808 A1 | 3/2007 | Novak et al. |
| 2007/0092485 A1 | 4/2007 | Novak et al. |
| 2007/0098682 A1 | 5/2007 | Novak et al. |
| 2007/0098683 A1 | 5/2007 | Novak et al. |
| 2007/0099269 A1 | 5/2007 | Novak et al. |
| 2007/0128189 A1 | 6/2007 | Sivakumar et al. |
| 2007/0166794 A1 | 7/2007 | Novak et al. |

FOREIGN PATENT DOCUMENTS

| | | |
|---|---|---|
| JP | 2005306757 | 4/2004 |
| WO | 99/61617 A1 | 12/1999 |
| WO | 2003087320 | 4/2003 |
| WO | 03/040313 A2 | 5/2003 |
| WO | 03/103589 A2 | 12/2003 |
| WO | 2004/032857 A2 | 4/2004 |
| WO | 2004/056392 A1 | 7/2004 |
| WO | 2004/083249 A2 | 9/2004 |
| WO | 2006057027 | 11/2004 |
| WO | 2005/037306 A1 | 4/2005 |

OTHER PUBLICATIONS

Brandt et al., "Generation of Antagonists by Amino Acid Replacement in the D-Helix of Human IL-21," *J. Leukocyte Biol.* S2001, abstr. 119, 2001, Publisher Not Available.
Kasaian et al., "IL21 blocks IL15-induced NK cell expansion and enhances IFNγ production," *J. Leukocyte Biol.* S2001, abstr. 76, 2001, Publisher Not Available.
Suto et al., "Interleukin 21 prevents antigen-induced IgE production by inhibiting germ line Cε transcription of IL-4-stimulated B cells," *Blood* 100(13):4565-4573, 2002.
Hecker et al., "Novel genetic variation of human interleukin-21 receptor is associated with elevated IgE levels, in females," *Genes and Immunity* 4:228-233, 2003.
Cohen et al., "Increased expression of CD132 and multiple IL-2 family receptors in psoriasis vulgaris," *J. Investigative Dermatol*, abstr. 0115, 2003, Publisher Not Available.
Caruso et al., "A Functional Role for Interleukin-21 in Promoting the Synthesis of the T-Cell Chemoattractant, MIP-3α, by Gut Epithelial Cells," *Gastroenterology* 132:166-175, 2007.

(Continued)

*Primary Examiner* — Bridget E Bunner
*Assistant Examiner* — Fozia Hamud
(74) *Attorney, Agent, or Firm* — Nelson Mullins Riley & Scarborough LLP; Jane E. Remillard, Esq.; Jeanne M. DiGiorgio, Esq.

(57) ABSTRACT

Monoclonal antibodies are identified that bind the IL-21 protein. These antibodies are used to identify regions of the IL-21 protein to where binding neutralizes IL-21 activity. Hybridomas and methods of producing anti-IL-21 monoclonal antibodies are described. The monoclonal antibodies are useful in treating IL-21-mediated diseases, which may include autoimmune and inflammatory diseases such as pancreatitis, type I diabetes (IDDM), Graves Disease, inflammatory bowel disease (IBD), Crohn's Disease, ulcerative colitis, irritable bowel syndrome, multiple sclerosis, rheumatoid arthritis, diverticulosis, systemic lupus erythematosus, psoriasis, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, graft versus host disease, transplant rejection, atopic dermatitis, anti-phospholipid syndrome, and asthma, and other autoimmune diseases.

6 Claims, No Drawings

OTHER PUBLICATIONS

Distler et al., "Inflammation-independent Overexpression of IL-21 Receptor mRNA in Keratinocytes from patients with Systemic Sclerosis,"*American College of Rheumatology Abstract Supplement*, abstr. 848, 2003, Publisher Not Available.

Brandt et al., "Interleukin-21 Inhibits Dendritic Cell-Mediated T Cell Activation and Induction of Contact Hypersensitivity In Vivo," *J. Invest. Dermatol. 121*(6):1379-82, 2003.

Brandt et al., "Interleukin-21 inhibits dendritic cell activation and maturation," *Blood 102*(12):4090-4098, 2003.

Distler, "Overexpression of IL-21 Receptor mRNA in the Epidermis of Patients with Systemic Sclerosis: Lessions from the SCID Mouse Transplantation Model," *Annals of the Rheumatic Diseases 63*(S. 1):107, OP0158, 2004.

Alexopoulos et al., "Tolerance Induction Using IL-21 Antagonizing Fusion Protein," *Experimental Tolerance Induction I*, Abstract #101, 2004.

O'Shea et al., "A New Modality for Immunosuppression: Targeting the JAK/STAT Pathway," *Nature Reviews 3*:555-564, 2004.

O'Shea et al., "Jak3 and the pathogenesis of severe combined immunodeficiency,"*Molecular Immunology 41*:727-737, 2004.

Wood et al., "IL-21 effects on human IgE production in response to IL-4 or IL-13," *Cellular Immunology 231*:133-145, 2004.

Stauber et al., "Crystal structure of the IL-2 signaling complex: Paradigm for a deterotrimeric cytokine receptor," *PNAS 103*(8):2788-1793, 2006.

Zhang et al., "Human IL-21 and IL-4 bind to partially overlapping epitopes of common γ-chain," *Biochem and Biophys Res Comm 300*:291-296, 2003.

Habib et al., "The common γ Chain (γc) Is a Required Signaling Component of the IL-21 Receptor and Supports IL-21-Indiced Cell Proliferation via JAK3,"*Biochemistry 41*:8725-8731, 2002.

Olosz et al., "Structural Basis for Binding Multiple Ligands by the Common Cytokine Receptorγ-Chain," *J. Biol. Chem. 277*(14):12047-12052, 2002.

Akamatsu, Norihiko et al., "Selected IL-21R Expression and Apoptosis Induction by IL-21 in Follicular Lymphoma," Blood, vol. 104(11):629a, Abstract No. 2284 (2004).

Aklilu, M. et al., "Depletion of normal B cells with rituximab as an adjunct to IL-2 therapy for renal cell carcinoma and melanoma," Annals of Oncology, vol. 15:1109-1114 (2004).

Bondensgaard, Kent et al., "The Existence of Multiple Conformers of Interleukin-21 Directs Engineering of a Superpotent Analogue," The Journal of Biological Chemistry, vol. 282(32):23326-23336 (2007).

Clegg, C.H. et al., "Therapeutic Opportunities for IL-21," International Cytokine Society Annual Meeting, European Cytokine Network, vol. 14(3) Suppl., p. 28, Abstract No. 66 (2003).

Funaro, Ada et al., "Monoclonal antibodies and therapy of human cancers," Biotechnology Advances, vol. 18:385-401 (2000).

Gitlitz, Barbara J. et al., "Cytokine-based therapy for metastatic renal cell cancer," Urologic Clinics of North America, vol. 30:589-600 (2003).

Hughes, S. et al., "Interleukin 21 efficacy in a mouse model of metastatic renal cell carcinoma," Journal of Clinical Oncology, vol. 22(14S), ASCO Annual Meeting Proceedings, Abstract No. 2598 (2004).

Hughes, Steve D. et al., "Mechanisms of IL-21 Enhancement of Rituximab Efficacy in a Lymphoma Xenograft Model," Blood, vol. 104(11):394s, Abstract No. 1404 (2004).

Kindsvogel, W. et al., "IL-21 enhances rituximab-mediated killing of B-lymphoma cell lines in vitro and in vivo," Journal of Clinical Oncology, vol. 22(14S), ASCO Annual Meeting Proceedings, Abstract No. 2581 (2004).

Ma, Hak-Ling et al., "IL-21 Activates Both Innate and Adaptive Immunity to Generate Potent Antitumor Responses that Require Perforin but Are Independent of IFN-gamma," The Journal of Immunology, vol. 171:608-615 (2003).

Mehta, Devangi S. et al., "IL-21 Induces the Apoptosis of Resting and Activated Primary B Cells," The Journal of Immunology, vol. 170:4111-4118 (2003).

Moroz, Adrianna et al., "IL-21 Enhances and Sustains CD8+ T Cell Responses to Achieve Durable Tumor Immunity: Comparative Evaluation of IL-2, IL-15, and IL-21," The Journal of Immunology, vol. 173:900-909 (2004).

Munshi, Nikhil C., "Recent Advances in the Management of Multiple Myeloma," Seminars in Hematology, vol. 41(2 Suppl. 4):21-26 (2004).

Nelson, Andrew et al., "Anti-Tumor Effects of Interleukin 21," Blood, vol. 100(11):158a, Abstract No. 593 (2002).

Nelson, Andrew et al., "Interleukin 21 has anti-tumor activity in animal models wthout the toxicity of IL-2," Proceedings of the American Association for Cancer Research, vol. 44, 2nd Ed., p. 562, Abstract No. 2863 (2003).

Ozaki, Katsutoshi et al., "Regulation of B Cell Differentiation and Plasma Cell Generation by IL-21, a Novel Inducer of Blimp-1 and Bcl-6," The Journal of Immunology, vol. 173:5361-5371 (2004).

Parrish-Novak, Julia et al., "Interleukin 21 and its receptor are involved in NK cell expansion and regulation of lymphocyte function," Nature, vol. 408:57-63 (2000).

Rastetter, William et al., "Rituximab: Expanding Role in Therapy for Lymphomas and Autoimmune Diseases," Annu. Rev. Med., vol. 55:477-503 (2004).

Ro, Torstein B. et al., "Interleukin-21 is a Growth and Survival Factor for Human Myeloma Cells," Blood, vol. 98 (11):773a, Abstract No. 3216 (2001).

Rowshani, Ajda T. et al., "Effects of CD25 monoclonal antibody on proliferative and effector functions of alloactivated human T cells in vitro," Eur. J. Immunol., vol. 34:882-889 (2004).

Sievers, E.L. et al., "IL-21 enhances trastuzumab-mediated killing of breast cancer cell lines in vitro," Breast Cancer Research and Treatment, vol. 88(Suppl. 1):5245, Abstract No. 6075 (2004).

Sivakumar, Pallavur et al., "Interleukin-21 Elicits Durable T and NK Cytotoxicity: Basic Biology to Clinical Trials," J. Immunother., vol. 27(6):556 (2004).

Sivakumar, Pallavur V. et al., "Interleukin-21 is a T-helper cytokine that regulates humoral immunity and cell-mediated anti-tumour responses," Immunology, vol. 112:117-182 (2004).

Stauber, Deborah et al., "Crystal structure of the IL-2 signaling complex: Paradigm for a heterotrimeric cytokine receptor," PNAS, vol. 103(8):2788-2793 (2006).

Strengell, Man et al., "IL-21 UP—Regulates the Expression of Genes Associated with Innate Immunity and Th1 Response," The Journal of Immunology, vol. 169:3600-3605 (2002).

Ueda, Maki et al., "Expression of Functional IL-21 Receptor on Adult T-Cell Leukemia (ATL) Cells," Blood, vol. 102 (11):893a, Abstract No. 3323 (2003).

Ueda, Maki et al., "Expression of functional interleukin-21 receptor on adult T-cell leukaemia cells," British Journal of Haematology, vol. 128:169-176 (2004).

Weidemann, Thomas et al., "Beyond Dimerization: A Membrane-dependent Activation Model for Interleukin-4 Receptor-mediated Signalling," J. Mol. Biol., vol. 366:1365-1373 (2007).

SEQUENCE LISTING

```
<160> NUMBER OF SEQ ID NOS: 8

<210> SEQ ID NO 1
<211> LENGTH: 21
<212> TYPE: PRT
<213> ORGANISM: Artificial Sequence
<220> FEATURE:
<223> OTHER INFORMATION: synthesized peptide
<220> FEATURE:
<221> NAME/KEY: VARIANT
<222> LOCATION: (1)...(1)
<223> OTHER INFORMATION: Xaa = pyroGlu
<220> FEATURE:
<221> NAME/KEY: AMIDATION
<222> LOCATION: (21)...(21)

<400> SEQUENCE: 1

Xaa Gln Asp Arg His Met Ile Arg Met Arg Gln Leu Ile Asp Ile Val
1               5                   10                  15

Asp Gln Leu Lys Cys
            20

<210> SEQ ID NO 2
<211> LENGTH: 19
<212> TYPE: PRT
<213> ORGANISM: Artificial Sequence
<220> FEATURE:
<223> OTHER INFORMATION: synthesized peptide

<400> SEQUENCE: 2

Asn Asp Leu Val Pro Glu Phe Leu Pro Ala Pro Glu Asp Val Glu Asn
1               5                   10                  15

Thr Asn Cys

<210> SEQ ID NO 3
```

```
<211> LENGTH: 26
<212> TYPE: PRT
<213> ORGANISM: Artificial Sequence
<220> FEATURE:
<223> OTHER INFORMATION: synthesized peptide
<220> FEATURE:
<221> NAME/KEY: AMIDATION
<222> LOCATION: (26)...(26)

<400> SEQUENCE: 3

Asn Val Ser Ile Lys Lys Leu Lys Arg Lys Pro Pro Ser Thr Asn Ala
 1               5                  10                  15
Gly Arg Arg Gln Lys His Arg Leu Thr Cys
            20                  25

<210> SEQ ID NO 4
<211> LENGTH: 29
<212> TYPE: PRT
<213> ORGANISM: Artificial Sequence
<220> FEATURE:
<223> OTHER INFORMATION: synthesized peptide
<220> FEATURE:
<221> NAME/KEY: AMIDATION
<222> LOCATION: (29)...(29)

<400> SEQUENCE: 4

Cys Asp Ser Tyr Glu Lys Lys Pro Pro Lys Glu Phe Leu Glu Arg Phe
 1               5                  10                  15
Lys Ser Leu Leu Gln Lys Met Ile His Gln His Leu Ser
            20                  25

<210> SEQ ID NO 5
<211> LENGTH: 642
<212> TYPE: DNA
<213> ORGANISM: Homo sapiens
<220> FEATURE:
<221> NAME/KEY: CDS
<222> LOCATION: (47)...(532)

<400> SEQUENCE: 5
gctgaagtga aaacgagacc aaggtctagc tctactgttg gtactt atg aga tcc         55
                                               Met Arg Ser
                                                1 agt cct ggc aac atg gag agg att gtc atc tgt ctg atg gtc atc ttc       103
Ser Pro Gly Asn Met Glu Arg Ile Val Ile Cys Leu Met Val Ile Phe
  5                  10                  15 ttg ggg aca ctg gtc cac aaa tca agc tcc caa ggt caa gat cgc cac       151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat       199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta       247
Tyr Val Asn Asp Leu Val Pro Glu Phe Leu Pro Ala Pro Glu Asp Val
             55                  60                  65 gag aca aac tgt gag tgg tca gct ttt tcc tgt ttt cag aag gcc caa       295
Glu Thr Asn Cys Glu Trp Ser Ala Phe Ser Cys Phe Gln Lys Ala Gln
         70                  75                  80 cta aag tca gca aat aca gga aac aat gaa agg ata atc aat gta tca       343
Leu Lys Ser Ala Asn Thr Gly Asn Asn Glu Arg Ile Ile Asn Val Ser
     85                  90                  95 att aaa aag ctg aag agg aaa cca cct tcc aca aat gca ggg aga aga       391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa       439
```

```
                                                                            -continued
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg    487
Pro Pro Lys Glu Phe Leu Glu Arg Phe Lys Ser Leu Leu Gln Lys Met
        135                 140                 145 att cat cag cat ctg tcc tct aga aca cac gga agt gaa gat tcc        532
Ile His Gln His Leu Ser Ser Arg Thr His Gly Ser Glu Asp Ser
150                 155                 160 tgaggatcta acttgcagtt ggacactatg ttacatactc taatatagta gtgaaagtca  592
tttctttgta ttccaagtgg aggagcccta ttaaattata aaagaaata              642

<210> SEQ ID NO 6
<211> LENGTH: 162
<212> TYPE: PRT
<213> ORGANISM: Homo sapiens

<400> SEQUENCE: 6

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 7
<211> LENGTH: 3072
<212> TYPE: DNA
<213> ORGANISM: Mus musculus
<220> FEATURE:
<221> NAME/KEY: CDS
<222> LOCATION: (54)...(491)

<400> SEQUENCE: 7
gagaaccaga ccaaggcccct gtcatcagct cctggagact cagttctggt ggc atg    56
                                                            Met
                                                            1 gag agg acc ctt gtc tgt ctg gta gtc atc ttc ttg ggg aca gtg gcc    104
Glu Arg Thr Leu Val Cys Leu Val Val Ile Phe Leu Gly Thr Val Ala
        5                   10                  15 cat aaa tca agc ccc caa ggg cca gat cgc ctc ctg att aga ctt cgt    152
His Lys Ser Ser Pro Gln Gly Pro Asp Arg Leu Leu Ile Arg Leu Arg
        20                  25                  30 cac ctt att gac att gtt gaa cag ctg aaa atc tat gaa aat gac ttg    200
His Leu Ile Asp Ile Val Glu Gln Leu Lys Ile Tyr Glu Asn Asp Leu
```

|  |  |
|---|---:|
| 35 40 45 | |
| gat cct gaa ctt cta tca gct cca caa gat gta aag ggg cac tgt gag<br>Asp Pro Glu Leu Leu Ser Ala Pro Gln Asp Val Lys Gly His Cys Glu<br>50 55 60 65 | 248 |
| cat gca gct ttt gcc tgt ttt cag aag gcc aaa ctc aag cca tca aac<br>His Ala Ala Phe Ala Cys Phe Gln Lys Ala Lys Leu Lys Pro Ser Asn<br>70 75 80 | 296 |
| cct gga aac aat aag aca ttc atc att gac ctc gtg gcc cag ctc agg<br>Pro Gly Asn Asn Lys Thr Phe Ile Ile Asp Leu Val Ala Gln Leu Arg<br>85 90 95 | 344 |
| agg agg ctg cct gcc agg agg gga gga aag aaa cag aag cac ata gct<br>Arg Arg Leu Pro Ala Arg Arg Gly Gly Lys Lys Gln Lys His Ile Ala<br>100 105 110 | 392 |
| aaa tgc cct tcc tgt gat tcg tat gag aaa agg aca ccc aaa gaa ttc<br>Lys Cys Pro Ser Cys Asp Ser Tyr Glu Lys Arg Thr Pro Lys Glu Phe<br>115 120 125 | 440 |
| cta gaa aga cta aaa tgg ctc ctt caa aag atg att cat cag cat ctc<br>Leu Glu Arg Leu Lys Trp Leu Leu Gln Lys Met Ile His Gln His Leu<br>130 135 140 145 | 488 |
| tcc tagaacacat aggacccgaa gattcctgag gatccgagaa gattcccgag<br>Ser | 541 |
| gactgaggag acgccggaca ctatagacgc tcacgaatgc aggagtacat cttgcctctt | 601 |
| gggattgcaa gtggagaagt acgatacgtt atgataagaa caactcagaa aagctatagg | 661 |
| ttaagatcct ttcgcccatt aactaagcag acattgtggt tccctgcaca gactccatgc | 721 |
| tgtcaacatg gaaaatctca actcaacaag agcccagctt cccgtgtcag ggatttctgg | 781 |
| tgcttctcaa gctgtggctt catcttattg cccaactgtg acattctttg attggaaggg | 841 |
| gaaaactaaa gcttttagca aaaatacagc tagggaattt gtcgatctgc gagagtaaga | 901 |
| cctcttatga tcctaacgga atgatgtaag ctggaaataa taagcataag atgaaattga | 961 |
| aaattgaagt ctttattctt taagaaaaac tttgtacttg aaagcatgtc tgaagagttt | 1021 |
| actcattacc acaaacatct agcatattga taactaacat ctttatactc tacaagagag | 1081 |
| gctttccaga taggtacagt ttttcttctc tattaggtct atcaaaattt aacctattat | 1141 |
| gagggtcacc cctggctttc actgtttttc taaagaggca agggtgtagt aagaagcagg | 1201 |
| cttaagttgc cttcctccca atgtcaagtt cctttataag ctaatagttt aatcttgtga | 1261 |
| agatggcaat gaaagcctgt ggaagtgcaa acctcactat cttctggagc caagtagaat | 1321 |
| tttcaagttt gtagctctca cctcaagtgg ttatgggtgt cctgtgatga atctgctagc | 1381 |
| tccagcctca gtctcctctc ccacatcctt tcctttcttt cctcttgaa acttctaaga | 1441 |
| aaaagcaatc caaacaagtt cagcacttaa gacacattgc atgcacactt ttgataagtt | 1501 |
| aaatccaacc atctatttaa aatcaaaatc aggagatgag ccaagagacc agaggttctg | 1561 |
| ttccagtttt aaacagactt ttactgaaca tcccaatctt ttaaccacag aggctaaatt | 1621 |
| gagcaaatag ttttgccatt tgatataatt tccaacagta tgtttcaatg tcaagttaaa | 1681 |
| aagtctacaa agctattttc cctggagtgg tatcatcgct ttgagaattt cttatggtta | 1741 |
| aaatggatct gagatccaag catggcctgg gggatggttt tgatctaagg aaaaaggtgt | 1801 |
| ctgtacctca cagtgccttt aaaacaagca gagatcccgt gtaccgccct aagatagcac | 1861 |
| agactagtgt taactgattc ccagaaaagt gtcacaatca gaaccaacgc attctcttaa | 1921 |
| actttaaaaa tatgtattgc aaagaacttg tgtaactgta aatgtgtgac tgttgatgac | 1981 |
| attatacaca catagcccac gtaagtgtcc aatggtgcta gcattggttg ctgagtttgc | 2041 |
| tgctcgaaag ctgaagcaga gatgcagtcc ttcacaaagc aatgatggac agagagggga | 2101 |

```
gtctccatgt tttattcttt tgttgtttct ggctgtgtaa ctgttgactt cttgacattg    2161
tgatttttat atttaagaca atgtatttat tttggtgtgt ttattgttct agccttttaa    2221
atcactgaca atttctaatc aagaagtaca aataattcaa tgcagcacag gctaagagct    2281
tgtatcgttt ggaaaagcca gtgaaggctt ctccactagc catgggaaag ctacgcttta    2341
gagtaaacta gacaaaattg cacagcagtc ttgaacctct ctgtgctcaa gactcagcca    2401
gtcctttgac attattgttc actgtgggtg ggaacacatt ggacctgaca cactgttgtg    2461
tgtccatgaa ggttgccact ggtgtaagct ttttttggtt ttcattctct tatctgtaga    2521
acaagaatgt ggggctttcc taagtctatt ctgtattta ttctgaactt cgtatgtctg     2581
agttttaatg ttttgagtac tcttacagga acacctgacc acactttga gttaaatttt      2641 atcccaagtg tgatatttag ttgttcaaaa agggaaggga tatacataca tacatacata    2701
catacataca tatatatata tatatataca tatatatata tatatatatg tatatatata    2761
tatatataga gagagagaga gagagagaga gagaaagaga gagaggttgt tgtaggtcat    2821
aggagttcag aggaaatcag ttatggccgt taatactgta gctgaaagtg ttttctttgt    2881
gaataaattc atagcattat tgatctatgt tattgctctg ttttatttac agtcacacct    2941
gagaatttag ttttaatatg aatgatgtac tttataactt aatgattatt tattatgtat    3001
ttggttttga atgtttgtgt tcatggcttc ttatttaaga cctgatcata ttaaatgcta    3061
cccagtccgg a                                                         3072
```

<210> SEQ ID NO 8
<211> LENGTH: 146
<212> TYPE: PRT
<213> ORGANISM: Mus musculus
<400> SEQUENCE: 8

```
Met Glu Arg Thr Leu Val Cys Leu Val Val Ile Phe Leu Gly Thr Val
 1               5                  10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145
```

US 8,222,374 B2

IL-21 ANTAGONISTS

REFERENCE TO RELATED APPLICATIONS

This application is a continuation of U.S. patent application Ser. No. 12/179,003, filed Jul. 24, 2008, issued as U.S. Pat. No. 7,923,539, which is a divisional U.S. patent application Ser. No. 11/563,928, filed Nov. 28, 2006, abandoned, which claims the benefit of U.S. Provisional Patent Application Ser. No. 60/740,154, filed Nov. 28, 2005, which are herein incorporated by reference.

BACKGROUND OF THE INVENTION

The immune system is the body's primary defense against diseases caused by pathogens, namely bacteria, viruses, fungi etc, as well as against diseases caused by abnormal growth of the body's own cells and tissues (i.e. cancerous tumors). Normally, the immune system is able to distinguish between the body's normal cells or "self" and foreign pathogens or abnormal cells or "non-self". The processes by which the immune system refrains from reacting to one's own body is called tolerance. Sometimes, the immune system loses the ability to recognize "self" as normal and the subsequent response directed against the tissue or cells, results in loss of tolerance, a state of autoimmunity. The pathologies resulting from autoimmunity often have serious clinical consequences and are one of the major health problems in the world, especially in developed nations.

Cytokines generally stimulate proliferation or differentiation of cells of the hematopoietic lineage or participate in the immune and inflammatory response mechanisms of the body. The interleukins are a family of cytokines that mediate immunological responses. Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the class II cytokine receptor family, based upon a characteristic 200 residue extracellular domain.

The present invention provides anti-IL-21 monoclonal antibodies and methods of using those antibodies that inhibit the symptoms and biological activities that manifest as autoimmune and inflammatory disorders and are associated with IL-21/IL-21 receptor interaction.

BRIEF DESCRIPTION OF THE INVENTION

In one aspect, the present invention provides a bin or family of antibodies that is capable of competition with a monoclonal antibody produced by the ATCC deposit 272.21.1.3.4.2 (ATCC Accession No. PTA-10395) for binding a human IL-21 antigen. In certain embodiments, the bin specifically binds to the epitope to which the monoclonal antibody produced by deposit 272.21.1.3.4.2 (ATCC Accession No. PTA-10395) binds.

In another aspect, the present invention provides a bin that is capable of competition with a monoclonal antibody produced by the ATCC deposit 268.5.1.11.42.1.4.3.9 (ATCC Accession No. PTA-10394) for binding a human IL-21 antigen. In certain embodiments, the bin specifically binds to the epitope to which the monoclonal antibody produced by deposit 268.5.1.11.42.1.4.3.9 (ATCC Accession No. PTA-10394) binds.

In another aspect, the present invention provides for a hybridoma cell designated ATCC deposit 272.21.1.3.4.2 (ATCC Accession No. PTA-10395; deposited Oct. 26, 2005; ATCC, 10801 University Blvd., Manassas, VA 20110-2209) for producing a monoclonal antibody.

In another aspect, the present invention provides for a hybridoma cell designated ATCC deposit 268.5.1.11.42.1.4.3.9 (ATCC Accession No. PTA-10394; deposited Oct. 26, 2005, ATCC, 10801 University Blvd., Manassas, VA 20110-2209) for producing a monoclonal antibody.

In a further aspect, the present invention provides a method of producing the antibodies described herein comprising: (a) providing a hybridoma capable of producing the monoclonal antibody; and (b) culturing the hybridoma under conditions that provide for the production the monoclonal antibody by the hybridoma.

In one aspect, the present invention provides an anti-IL-21 monoclonal antibody that binds to an antigen region of human IL-21. In certain embodiments, the monoclonal antibody binds to an antigenic region of IL-21 that is shown in SEQ ID NO: 6 from amino acid residues 97-122. In another embodiment, the monoclonal antibody binds an antigenic region as shown in SEQ ID NO: 6 from amino acid residues 145 to 148. In another embodiment, the monoclonal antibody binds an antigenic region as shown in SEQ ID NO: 6 from amino acid residues 154 to 162. In another embodiment, the monoclonal antibody binds an antigen region as shown in SEQ ID NO: 6 from amino acid residues 30 to 50. In another embodiment, the monoclonal antibody binds to an antigen region as shown in SEQ ID NO: 6 from amino acid residues 40 to 50. Additional embodiments include monoclonal antibodies as described herein that can be shown to neutralize a human IL-21 protein activity, binds a human IL-21-Fc protein, bind a human mutein Fc protein, where the mutations are at Gln 145 and/or Ile148 of SEQ ID NO: 6, or bind a mouse IL-21-mouse Fc fusion protein. Generally, the monoclonal antibodies of the present invention bind two or more IL-21 proteins.

In other aspects, the monoclonal antibody specifically binds to the epitope to which monoclonal antibody produced by 272.21.1.3.4.2 (ATCC Accession No. PTA-10395) binds. In other embodiments, the monoclonal antibody specifically binds to the epitope to which monoclonal antibody produced by 268.5.1.11.42.1.4.3.9 (ATCC Accession No. PTA-10394) binds. The monoclonal antibodies of the present invention may also be labeled with a detectable marker and the detectable marker can be selected from, but is not limited to, radioactive isotopes, enzymes, dyes and biotins.

In another aspect, the present invention provides a bin (or group of antibodies) that is capable of competition with monoclonal antibody produced by 272.21.1.3.4.2 (ATCC Accession No. PTA-10395) for binding a human IL-21 antigen.

Another aspect of the present invention provides a bin that is capable of competition with monoclonal antibody produced by 268.5.1.11.42.1.4.3.9 (ATCC Accession No. PTA-10394) for binding a human IL-21 antigen.

Also included in the present invention are hybridomas producing the claimed monoclonal antibodies.

The present invention provides a method of producing the claimed monoclonal antibodies comprising: (a) providing a hybridoma capapble of producing the monoclonal antibody; and (b) culturing the hybridoma under conditions that provide for production of the monoclonal antibody by the hybridoma.

In another aspect, the present invention provides a method of treating an autoimmune disease comprising administering a therapeutically effective amount of the claimed anti-IL-21 monoclonal antibodies to a patient. In certain embodiments, the autoimmune disease is selected from the group consisting of pancreatitis, type I diabetes (IDDM), Graves Disease, inflammatory bowel disease (IBD), Crohn's Disease, ulcerative colitis, irritable bowel syndrome, multiple sclerosis, rheumatoid arthritis, diverticulosis, systemic lupus erythematosus, psoriasis, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, graft versous host disease, transplant rejection, atopic dermatitis, anti-phospholipid syndrome, and asthma, and other autoimmune diseases.

The present invention also provides a method of inhibiting or reducing an IL-21-mediated disorder comprising administering an anti-IL-21 monoclonal antibody in an amount sufficient to inhibit or reduce IL-21 mediated biological activity in the subject.

DESCRIPTION OF THE INVENTION

The following definitions are provided to facilitate understanding of the inventions described herein.

The term "antibody" or "antibody peptide(s)" refers to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "variant" anti-IL-21 antibody, refers herein to a molecule which differs in amino acid sequence from a "parent" anti-IL-21 antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical to the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL-21 and preferably has properties which are superior to those of the parent antibody. For example, the variant may have a stronger binding affinity, enhanced ability to inhibit IL-21-induced stimulation of immune cells. To analyze such properties, one should compare a Fab form of the variant to a Fab form of the parent antibody or a full length form of the variant to a full length form of the parent antibody, for example, since it has been found that the format of the anti-IL-21 antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The term "parent antibody" as used herein refers to an antibody which is encoded by an amino acid sequence used for the preparation of the variant. Preferably, the parent antibody has a human framework region and, if present, has human antibody constant region(s). For example, the parent antibody may be a humanized or human antibody.

The term "agonist" refers to any compound including a protein, polypeptide, peptide, antibody, antibody fragment, large molecule, or small molecule (less than 10 kD), that increases the activity, activation or function of another molecule. IL-21 agonists cause, for example: stimulation of NK cells, T cell subsets and B cell subsets and dendritic cells.

The term "antagonist" refers to any compound including a protein, polypeptide, peptide, antibody, antibody fragment, large molecule, or small molecule (less than 10 kD), that decreases the activity, activation or function of another molecule. IL-21 antagonists cause: decreased immune function of NK cells, T cell subsets and B cell subsets and dendritic cells; bind IL-21 such that the interaction of IL-21 protein is blocked, inhibited, reduced, antagonized or neutralized.

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, *Clin. Exp. Immunol* 79:315-321 (1990); Kostelny et al., *J. Immunol.* 148:1547-1553 (1992).

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used.

The term "effective neutralizing titer" as used herein refers to the amount of antibody which corresponds to the amount present in the serum of animals (human or cotton rat) that has been shown to be either clinically efficacious (in humans) or to reduce virus by 99% in, for example, cotton rats. The 99% reduction is defined by a specific challenge of, e.g., $10^3$ pfu, $10^4$ pfu, $10^5$ pfu, $10^6$ pfu, $10^7$ pfu, $10^8$ pfu, or $10^9$ pfu) of RSV.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-21 epitope" as used herein refers to a portion of a IL-21 polypeptide having antigenic or immunogenic activity in an animal, preferably in a mammal, and most preferably in a mouse or a human. An epitope having immunogenic activity is a portion of a IL-21 polypeptide that elicits an antibody response in an animal. An epitope having antigenic activity is a portion of a IL-21 polypeptide to which an antibody immunospecifically binds as determined by any method well known in the art, for example, by immunoassays. Antigenic epitopes need not necessarily be immunogenic.

The term "epitope tagged" when used herein refers to the anti-IL-21 antibody fused to an "epitope tag". The epitope tag polypeptide has enough residues to provide an epitope against which an antibody can be made, yet is short enough such that it does not interfere with activity of the IL-21 antibody. The epitope tag preferably is sufficiently unique so that the antibody does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al. *Mol. Cell. Biol.* 8:2159-2165 (1988)); the c-myc tag and the 8F9, 3C7, 6E10, G4, B7 and 9E10 antibodies thereto (Evan et al., *Mol. Cell. Biol.* 5(12):3610-3616 (1985)); and the Herpes Simplex virus glycoprotein D (gD) tag and its antibody (Paborsky et al., *Protein Engineering* 3(6):547-553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "fragment" as used herein refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues of the amino acid sequence of a IL-21 polypeptide or an antibody that immunospecifically binds to a IL-21 polypeptide.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the $NH_2$-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7.

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, *J. Mol. Biol.* 196: 901-917, 1987) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

As used herein, the term "human antibody" includes and antibody that has an amino acid sequence of a human immunoglobulin and includes antibodies isolated from human immunoglobulin libraries or from animals transgenic for one or more human immunoglobulin and that do not express endogenous immunoglobulins, as described, for example, by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and (Fab)$_2$, as well as diabodies, linear antibodies, multivalent or multispecific hybrid antibodies (as described above and in detail in: Lanzavecchia et al., *Eur. J. Immunol.* 17, 105 (1987)) and in single chains (e.g., Huston et al., *Proc. Natl. Acad. Sci. U.S.A.*, 85 5879-5883 (1988) and Bird et al., *Science*, 242:423-426 (1988), which are incorporated herein by reference). (See, generally, Hood et al., "Immunology", Benjamin, N.Y., 2nd ed. (1984), and Hunkapiller and Hood, *Nature*, 323:15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the VH and VL domains which enables it to form the desired structure which would allow for antigen binding Single chain antibodies are discussed in detail by Pluckthun in *The Pharmacology of Monoclonal Antibodies*, vol. 113, Rosenburg and Moore eds. Springer-Verlag, New York, pp. 269-315 (1994); see also International Patent Application Publication No. WO 88/01649 and U.S. Pat. Nos. 4,946,778 and 5,260,203, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

The term "diabodies" refers to small antibody fragments with two antigen-binding sites, which fragments comprise a heavy chain variable domain (V$_H$) connected to a light chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The term "linear antibodies" refers to the antibodies described in Zapata et al. *Protein Eng.* 8(10):1057-1062 (1995). Briefly, these antibodies comprise a pair of tandem Fd segments (V$_H$-C$_{H1}$-V$_H$-C$_{H1}$) which form a pair of antigen binding regions. Linear antibodies can be bispecific or monospecific.

The term "immunologically functional immunoglobulin fragment" as used herein refers to a polypeptide fragment that contains at least the variable domains of the immunoglobulin heavy and light chains. An immunologically functional immunoglobulin fragment of the invention is capable of binding to a ligand, preventing binding of the ligand to its receptor, interrupting the biological response resulting from ligand binding to the receptor, or any combination thereof. Preferably, an immunologically functional immunoglobulin fragment of the invention binds specifically to IL-21.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The present invention provides monoclonal antibodies and antibody fragments that specifically bind with IL-21 proteins and polypeptides. Human and mouse IL-21 polypeptides, proteins and polynucleotides encoding the polypeptides are disclosed in Parrish-Novak et al., *Nature* 408:57-63, 2003, U.S. Pat. Nos. 6,307,024 and 6,686,178 and WO 04/055168. Exemplary antibodies include neutralizing antibodies, and may be murine monoclonal antibodies, humanized antibodies derived from murine monoclonal antibodies, and human monoclonal antibodies. Illustrative antibody fragments include F(ab')2, F(ab)$_2$, Fab', Fab, Fv, scFv, and minimal recognition units. Neutralizing antibodies preferably bind IL-21 such that the interaction of IL-21 protein is blocked, inhibited, reduced, antagonized or neutralized. Described herein are epitopes and structural and functional characteristics defining regions of the human IL-21 protein that have been identified as targets for a therapeutic monoclonal antibody. Exemplary mouse anti-human IL-21 monoclonal antibodies and rat anti-human monoclonal antibodies and pools of these monoclonal antibodies with the ability to bind wild-type human IL-21, a mutant IL-21 protein and/or peptide regions of human IL-21 are presented. The present invention further includes compositions comprising a carrier and a peptide, polypeptide, or antibody described herein.

Thus, the present invention provides that antagonists to IL-21 activity, such as anti-IL-21 antibodies, which are useful in therapeutic treatment of inflammatory diseases. For example, anti-IL-21 antibodies are useful in the treatment of pancreatitis, type I diabetes (IDDM), Graves Disease, inflammatory bowel disease (IBD), Crohn's Disease, ulcerative colitis, irritable bowel syndrome, multiple sclerosis, rheumatoid arthritis, diverticulosis, systemic lupus erythematosus, psoriasis, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, graft versus host disease, transplant rejection, atopic dermatitis, anti-phospholipid syndrome, and asthma, and other autoimmune diseases, or other diseases mediated by IL-21 and IL-21 receptor agonists.

The present invention also includes genetically altered antibodies that are functionally equivalent to the above-described antibodies. Modified antibodies providing improved stability and/or therapeutic efficacy are preferred. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Antibodies of the present invention can be can be modified post-translationally (e.g., acetylation, and phosphorylation) or can be modified synthetically (e.g., the attachment of a labeling group).

The genetically altered antibodies also include chimeric antibodies that derived from the anti-IL-21 antibodies. Preferably, the chimeric antibodies comprise a variable region derived from a mouse or rat and a constant region derived from a human so that the chimeric antibody has a longer half-life and is less immunogenic when administered to a human subject. The method of making chimeric antibodies is known in the art. The variable regions of these antibodies can be connected with a constant region of a human IgG to form the desired chimeric antibody.

Preferably, the genetically altered anti-IL-21 antibodies used in the present invention include humanized version of the antibodies described herein. In certain embodiments, the humanized antibody comprising CDRs of a mouse donor immunoglobulin and heavy chain and light chain frameworks of a human acceptor immunoglobulin. The method of making humanized antibody is disclosed in U.S. Pat. Nos. 5,301,101; 5,585,089; 5,693,762; and 6,180,370 (each of which is incorporated by reference in its entirety). The CDRs of these antibodies can then be grafted to any selected human frameworks, which are known in the art, to generate the desired humanized antibody.

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, or by size in contiguous amino acid residues. Antibodies of the present invention may also be described or specified in terms of their cross-reactivity. Antibodies that do not bind any other analog, ortholog, or homolog of a polypeptide of the present invention are included.

Epitope binning refers to the use of competitive binding assays to identify pairs of antibodies that are, or are not, capable of binding IL-21 protein simultaneously thereby identifying antibodies that bind to the same, or overlapping epitopes on protein. Families of antibodies (or bins) having the same binding specificity can then be used to define specific epitopes on IL-21. Epitope binning experiments provide evidence that antigenically distinct epitopes are present. However, by themselves, they do not identify, or "map" the epitope to a specific amino acid sequence or location on the IL-21 protein molecule.

Competition for binding can be evaluated for any pair of antibodies or fragments. For example, using the appropriate detection reagents, the binding specificity of antibodies or binding fragments from any species/source can be compared to the binding specificity of the monoclonal antibodies disclosed herein. Epitope binning can be performed with "isolated antibodies" or with cell culture supernatants. Frequently binning is performed with first round clonal supernatants to guide the choice of clones to be developed further. The antibodies to be compared should have substantially homogeneous antigen binding domains. In the case of "bispecific" or "bifunctional" antibodies the binding specificity of the two different binding sites need to be evaluated or binned independently.

The present invention features both receptor-specific antibodies and ligand-specific antibodies. In addition to competitive binding of antibodies, epitope binning can also be used to identify antibodies to either a receptor or a ligand that competitively interfere with the binning of a ligand and its receptor. Frequently, favorable properties, of a family (or bin) of antibodies can correlated with a binding to a specific epitope defined by the epitope bin.

Competitive binding experiments do not directly measure the binding affinity, however the antibodies to be tested must bind sufficiently strongly to act as competitors. Generally experimental conditions are designed to minimize the effects of differences in binding affinity.

Anti-Antigen IL-21 antibodies may also be useful in diagnostic assays for IL-21 protein, e.g., detecting its expression in specific cells, tissues, or serum. Antibodies assigned to different bins and capable of binding to different immunogenic portions, or epitopes, of IL-21 may be used as the reagents for sandwich assays. In a sandwich assay, the test sample analyte is captured by a first antibody which is immobilized on a solid support, and thereafter detected by a second antibody that also binds to the analyte, thus forming an insoluble three-part complex. See, e.g., U.S. Pat. No. 4,376, 110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the present invention may be assayed for specific binding by any method known in the art. Many different competitive binding assay format(s) can be used for epitope binning. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, *Current Protocols in Molecular Biology*, Vol. 1, John Wiley & Sons, Inc., New York). Exemplary immunoassays are described briefly below (but are not intended by way of limitation). Additionally, a routine cross-blocking assay such as that described in *Antibodies, A Laboratory Manual*, Cold Spring Harbor Laboratory, Ed Harlow and David Lane (1988), can be performed.

The Biacore is only one of a variety of assay formats that are routinely used to epitope bin panels of monoclonal antibodies. Many references (e.g. The Epitope Mapping Protocols, *Methods in Molecular Biology*, Volume 6.6 Glenn E. Morris ed.) describe alternative methods that could be used to bin antibodies and would be expected to provide identical information regarding the binding specificity of the antibodies to IL-21 protein. When using the Biacore system, epitope binning experiments are performed with soluble, native antigen. Epitope binning studies can be performed on a Biacore10000 system (Biacore, Uppsalla Sweden). BIAlogue® v. 1.2 software can be used for programming run methods. For the example of using the Biacore to bin mouse monoclonal antibodies raised against IL-21, polyclonal goat anti-Mouse IgG Fc antibody (Jackson ImmunoResearch Laboratories, West Grove, Pa.) can be covalently immobilized to a Biacore® CM5 sensor chip and used to bind (capture) the primary monoclonal antibody of test series to the chip. Unoccupied Fc binding sites on the chip are then blocked using a polyclonal IgG Fc fragment (Jackson ImmunoResearch Laboratories, West Grove, Pa.). Subsequently, IL-21 protein is injected and allowed to specifically bind to the captured primary monoclonal antibody. The Biacore instrument measures the mass of protein bound to the sensor chip, and the binding of both the primary antibody and IL-21 antigen can be verified for each cycle. Following the binding of the primary antibody and antigen to the chip, soluble secondary antibody is injected and allowed to bind to the pre-bound antigen. If the secondary monoclonal antibody is capable of binding the IL-21 antigen simultaneously with the primary monoclonal antibody, its binding is detected by the Biacore. If, however, the secondary monoclonal antibody is not capable of binding the IL-21 antigen simultaneously with the primary monoclonal antibody, no additional binding is detected. Each monoclonal antibody is tested against itself as a negative control to establish the level of the background (no-binding) signal.

A label-free competitive ELISA format (LFC-ELISA) can also be used to bin antibodies. This method is described by Nagata et al., *J. Immuno Methods* 292:141-155, 2004. This method for epitope binning utilized biotinylated IL-21. For the example of binning mouse monoclonal antibodies raised against IL-21, microtiter plates are coated at 100 μL/well with 1 μg/mL of a goat anti-mouse IgG Fc-γ specific antibody (Jackson ImmunoResearch) diluted in ELISA B (PBS, 0.1% Tween 20, 1% BSA). After binding of this coating antibody for 3 hours at ambient temperature, each mAb-containing conditioned media is diluted in ELISA B to yield an approximate mAb concentration of 0.5 μg/mL and allowed to bind to the goat anti-mouse IgG coated plates overnight at 4° C. (mAb#1). In parallel, a second set of conditioned medias (mAb#2) are diluted in polystyrene test tubes to approximately 0.5 μg/mL mAb in ELISA B, mixed with 50 ng/mL biotinylated IL-21 antigen, and incubated overnight at 4° C. After incubation of mAb#1 with the coating antibody, the plates are blocked with an unrelated antibody to saturate unoccupied binding sites on the plate. The mAb#2-biotin-IL-21 mixtures are added to the plate and allowed to bind. As a control for (non-competition) in the assay, 50 ng/mL biotinylated IL-21 is added directly (without pre-incubation with mAb#2) to wells containing immobilized mAb#1. After incubation with the biotinylated-IL-21-mAb#2 complex, streptavidin-HRP (Pierce, Rockford, Ill.) is added to the plate at 0.5 μg/mL. The plates are developed with TMB substrate (BioFX Laboratories, Owings Mills, Md.), and the absorbance of the individual wells at 450 nm is measured with a plate reader (Molecular Devices SpectraMax®340, Sunnyvale, Calif.). If mAb#1 binds to a different epitope from mAb#2, the biotin-IL-21-mAb#2 complex will bind to the plate resulting in a high absorbance reading. If mAb#1 binds to the same epitope as mAb#2, the biotin-IL-21-MAb#2 complex will not bind to the plate resulting in a low absorbance reading.

Antibodies of the present invention act as antagonists of IL-21. For example, the present invention includes antibodies which disrupt IL-21's receptor/ligand interactions either partially or fully. The invention features ligand-specific antibodies that prevent receptor activation. The invention includes neutralizing antibodies which bind the ligand and prevent binding of the ligand to the receptor, as well as antibodies which bind the ligand, thereby preventing receptor activation, but do not prevent the ligand from binding the receptor. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot or luminex based analysis (for example, as described supra). In specific embodiments, antibodies are provided that inhibit ligand or receptor activity by at least 90%, at least 80%, at least 70%, at least 60%, or at least 50% of the activity in absence of the antibody.

Production of Anti-IL-21 Antibodies

Antibodies to IL-21 can be obtained, for example, using the product of a IL-21 expression vector or IL-21 isolated from a natural source as an antigen. Particularly useful anti-IL-21 antibodies "bind specifically" with IL-21. Antibodies are considered to be specifically binding if the antibodies exhibit at least one of the following two properties: (1) antibodies bind to IL-21 with a threshold level of binding activity, and (2) antibodies do not significantly cross-react with polypeptides related to IL-21.

With regard to the first characteristic, antibodies specifically bind if they bind to a IL-21 polypeptide, peptide or epitope with a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 1949) or using a commercially available biosensor instrument (BIAcore, Pharmacia Biosensor, Piscataway, N.J.). With regard to the second characteristic, antibodies do not significantly cross-react with related polypeptide molecules, for example, if they detect IL-21, but not other known polypeptides using a standard Western blot analysis or capture ELISA. Examples of known related polypeptides include known members of the IL-2 family.

Anti-IL-21 antibodies can be produced using antigenic IL-21 epitope-bearing peptides and polypeptides. Antigenic epitope-bearing peptides and polypeptides of the present invention contain a sequence of at least nine, or between 15 to about 30 amino acids contained within SEQ ID NO:2 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with IL-21. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

Monoclonal anti-IL-21 antibodies can be generated by methods known to those skilled in the art. Rodent monoclonal antibodies to specific antigens may be obtained by known methods (see, for example, Kohler et al., *Nature* 256:495 (1975), Coligan et al. (eds.), Current Protocols in Immunology, Vol. 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)).

Selection of binders from the display of a library of antibody fragments is an in vitro alternative to the development of monoclonal antibodies. The principle of display technology is establishment of a physical connection between a binding moiety and the encoding genetic material. This concept has been used in a number of modes from display of protein and peptide libraries on surfaces of bacteriophage, bacteria, and yeast to the display of proteins attached to ribosomes in vitro (see for example Rothe et al., *FASEB J.* 20:1599 (2006)). The display of antibodies on the surface on single-stranded bacteriophage is the most highly developed of these technologies. The typical method used for antibody display is to fuse either the single chain Fv fragment or the heavy chain Fd (heavy chain portion of a Fab) with the gene III protein of the phage. Antibody libraries can be naïve, representing the natural immune repertoire, or semi-synthetic, consisting of frameworks taken from native human templates combined with synthetic CDR sequence libraries to increase diversity. Phage with specific binding activities can be isolated from random libraries of antibody fragments (particularly Fab and scFv) or peptides after repeated rounds of growth and selection (see, for example, Hoogenboom, *Nature Biotech.* 23:1105 (2005).)

In a further embodiment, antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety. In yet a further embodiment, antibodies or antibody fragments can be isolated from antibody phage libraries generated using the techniques described in McCafferty et al., *Nature*, 348: 552-554 (1990). Clackson et al., *Nature*, 352: 624-628 (1991) and Marks et al., *J. Mol. Biol.*, 222: 581-597 (1991) describe the isolation of murine and human antibodies, respectively, using phage libraries. Subsequent publications describe the production of high affinity (nM range) human antibodies by chain shuffling (Marks et al., *Bio/Technology*, 10: 779-783 (1992)), as well as combinatorial infection and in vivo recombination as a strategy for constructing very large phage libraries (Waterhouse et al., *Nuc. Acids. Res.*, 21: 2265-2266 (1993)). Thus, these techniques are viable alternatives to traditional monoclonal antibody hybridoma techniques for isolation of monoclonal antibodies.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869, 1992; and Sawai et al., *AJRI* 34:26-34, 1995; and Better et al., *Science* 240:1041-1043, 1988 (all references incorporated by reference in their entireties).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (*Int. Rev. Immunol* 13:65-93, 1995).

For a detailed discussion of this technology for producing human antibodies and human monoclonal antibodies and protocols for producing such antibodies, see, e.g., Jakobovits et al., *Proc. Natl. Acad. Sci. USA*, 90: 2551 (1993); Jakobovits et al., *Nature*, 362: 255-258 (1993); Bruggermann et al., *Year in Immuno.*, 7:33 (1993); PCT publications WO 98/24893; WO 96/34096; WO 96/33735; U.S. Pat. Nos. 5,413,923; 5,625, 126; 5,633,425; 5,569,825; 5,661,016; 5,545,806; 5,814,318; and 5,939,598, which are incorporated by reference herein in their entirety. In addition, companies such as Medarex, Inc. (Princeton, N.J.) and Genpharm (San Jose, Calif.) can be engaged to provide human antibodies directed against a selected antigen using technology similar to that described above. See, e.g. U.S. Pat. No. 7,135,287.

The antibodies of the invention can be produced by any method known in the art for the synthesis of antibodies, in particular, by chemical synthesis or preferably, by recombinant expression techniques. Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., MPSV, CMV, the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus, CMV enhancer or MPSV promoter is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, *Nucleic Acids Res.* 13:3101-3109, 1985; Van Heeke & Schuster, *J. Biol. Chem.* 24:5503-5509, 1989); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359, 1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544, 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:202, 1992), and adenine phosphoribosyltransferase (Lowy et al., *Cell* 22:817, 1980) genes can be employed in tk–, hgprt– or aprt–cells, respectively. Also, antimetabolite resistance can be used as the basis of selection for the following genes: dhfr, which confers resistance to methotrexate (Wigler et al., *Proc. Natl. Acad. Sci. USA* 77:357, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Wu and Wu, *Biotherapy* 3:87-95, 1991; Tolstoshev, *Ann. Rev. Pharmacol. Toxicol.* 32:573-596, 1993; Mulligan, *Science* 260:926-932, 1993; and Morgan and Anderson, *Ann. Rev. Biochem.* 62:191-217, 1993; *TIB TECH* 11(5):155-215), May, 1993; and hygro, which confers resistance to hygromycin (Santerre et al., *Gene* 30:147, 1984). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., *J. Mol. Biol.* 150:1, 1981; which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257, 1983).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, *Nature* 322:52, 1986; Kohler, *Proc. Natl. Acad. Sci. USA* 77:2197, 1980). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

For particular uses, it may be desirable to prepare fragments of anti-IL-21 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., Arch *Biochem. Biophys.* 89:230, 1960; Porter, *Biochem. J.* 73:119, 1959; Edelman et al., in Methods in Enzymology Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of VH and VL chains. This association can be noncovalent, as described by Inbar et al., *Proc. Nat'l Acad. Sci. USA* 69:2659, 1972. Alternatively, the variable chains can be linked by an intermolecular disulfide bond or cross-linked by chemicals such as glutaraldehyde (see, for example, Sandhu, *Crit. Rev. Biotech.* 12:437, 1992).

The Fv fragments may comprise VH and VL chains which are connected by a peptide linker. These single-chain antigen binding proteins (scFv) are prepared by constructing a structural gene comprising DNA sequences encoding the VH and VL domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., Methods: A Companion to Methods in Enzymology 2:97 (1991) (also see, Bird et al., *Science* 242:423, 1988, Ladner et al., U.S. Pat. No. 4,946,778, Pack et al., *Bio/Technology* 11:1271, 1993, and Sandhu, supra).

As an illustration, a scFV can be obtained by exposing lymphocytes to IL-21 polypeptide in vitro, and selecting antibody display libraries in phage or similar vectors (for instance, through use of immobilized or labeled IL-21 protein or peptide). Genes encoding polypeptides having potential IL-21 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., Phage Display of Peptides and Proteins (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the IL-21 sequences disclosed herein to identify proteins which bind to IL-21.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Methods in Enzymology 2:106 (1991), Courtenay-Luck, "Genetic Manipulation of Monoclonal Antibodies," in Monoclonal Antibodies: Production, Engineering and Clinical Application, Ritter et al. (eds.), page 166 (Cambridge University Press 1995), and Ward et al., "Genetic Manipulation and Expression of Antibodies," in Monoclonal Antibodies: Principles and Applications, Birch et al., (eds.), page 137 (Wiley-Liss, Inc. 1995)).

Alternatively, an anti-IL-21 antibody may be derived from a "humanized" monoclonal antibody. Humanized monoclonal antibodies are produced by transferring mouse or rat complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986; Carter et al., *Proc. Nat'l Acad. Sci. USA* 89:4285, 1992; Sandhu, *Crit. Rev. Biotech.* 12:437, 1992; Singer et al., *J. Immun.* 150:2844, 1993; Sudhir (ed.), Antibody Engineering Protocols (Humana Press, Inc. 1995), Kelley, "Engineering Therapeutic Antibodies," in Protein Engineering Principles and Practice, Cleland et al. (eds.), pages 399-434 (John Wiley & Sons, Inc. 1996), and by Queen et al., U.S. Pat. No. 5,693,762.

It is also possible to construct alternative frameworks by using a collection of monomeric proteins to form a monomer domain. These monomer domains can be small enough to penetrate tissues. The monomer domains can be naturally-occurring or non-natural vaiants or combination thereof. Monomer domains can form multimers of two more domains. The monomer domain binds a position, analogous to epitopes described herein, on a target molecule. In some cases, the multimer can be formed from variety of monomer domains. (See, e.g. U.S. Patent Application 2004-0132028 and U.S. Patent Application 2006-0177831.)

The antibodies of the present invention include derivatives that are modified, i.e, by the covalent attachment of any type of molecule to the antibody such that covalent attachment does not prevent the antibody from binding IL-21 or preventing receptor activation. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

An anti-IL-21 antibody can be conjugated with a detectable label to form an anti-IL-21 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below. The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-IL-21 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

It is also possible that anti-IL-21 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-IL-21 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-IL-21 immunoconjugates can be detectably labeled by linking an anti-IL-21 antibody component to an enzyme. When the anti-IL-21-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-IL-21 antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-IL-21 antibodies that have been conjugated with avidin, streptavidin, and biotin (see, for example, Wilchek et al. (eds.), "Avidin-Biotin Technology," Methods In Enzymology, Vol. 184 (Academic Press 1990), and Bayer et al., "Immunochemical Applications of Avidin-Biotin Technology," in Methods In Molecular Biology, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Pharmaceutical Compositions

The present invention further includes pharmaceutical compositions, comprising a pharmaceutically acceptable carrier and a polypeptide or antibody described herein. The pharmaceutical composition can include additional therapeutic agents, including but not limited to cytotoxic agents a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). For example, the pharmaceutical composition can comprise a protein or polypeptide possessing a desired biological activity. Such proteins may include, for example, a toxin such as abrin, ricin A, pseudomonas exotoxin, or diphtheria toxin; a protein such as tumor necrosis factor, α-IFN, β-IFN, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

For purposes of therapy, anti-IL-21 antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising anti-IL-21 antibody can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287, 1997; Murahashi et al., *Biol. Pharm. Bull.* 20:259, 1997). Similarly, Wu et al., *Hepatology* 27:772, 1998, have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259, 1997). Polyaconitylated human serum albumin liposomes provide another approach for targeting liposomes to liver cells (Kamps et al., *Proc. Nat'l Acad. Sci. USA* 94:11681, 1997). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99, 1998). After plasma elimination of free antibody, streptavidin-conjugated liposomes are administered. In another approach, targeting antibodies are directly attached to liposomes (Harasym et al., ibid. (1998)).

Polypeptides and antibodies can be encapsulated within liposomes using standard techniques of protein microencapsulation (see, for example, Anderson et al., *Infect. Immun.* 31:1099, 1981, Anderson et al., *Cancer Res.* 50:1853, 1990, and Cohen et al., *Biochim. Biophys. Acta* 1063:95, 1991, Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124, 1987). As noted above, therapeutically useful liposomes may contain a variety of components. For example, liposomes may comprise lipid derivatives of poly(ethylene glycol) (Allen et al., *Biochim. Biophys. Acta* 1150:9, 1993).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332, 1995; Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161, 1998; Putney and Burke, *Nature Biotechnology* 16:153, 1998; Putney, *Curr. Opin. Chem. Biol.* 2:548, 1998). Polyethylene glycol (PEG)-coated nanospheres can also provide carriers for intravenous administration of therapeutic proteins (see, for example, Gref et al., *Pharm. Biotechnol.* 10:167, 1997).

Other dosage forms can be devised by those skilled in the art, as shown, for example, by Ansel and Popovich, *Pharmaceutical Dosage Forms and Drug Delivery Systems,* 5th Edition (Lea & Febiger 1990), Gennaro (ed.), *Remington's Pharmaceutical Sciences,* 19th Edition (Mack Publishing Company 1995), and by Ranade and Hollinger, *Drug Delivery Systems* (CRC Press 1996).

Pharmaceutical compositions may be supplied as a kit comprising a container that comprises a neutralizing anti-IL-21 antibody). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition.

A pharmaceutical composition comprising anti-IL-21 antibodies can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239, 1997; Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Therapeutic Uses for Anti-IL-21 Antibodies

IL-21 is a $CD4^+$ T cell-derived cytokine that is important for optimal $CD8^+$ T cell mediated immunity, NK cell activation, and optimal humoral responses, such as antibody production and B cell maturation. IL-21 has been shown to induce a number of proinflammatory chemokines and cytokines, such as IL-18, IL-15, IL-5, IL-6, TNFR11, sCD25, and RANTES. IL-21 also induces an acute phase response in non-human primates and humans. Increased expression of IL-21 receptor has been shown in epidermis in patients with systemic sclerosis (Distler et al., *Arthritis & Rheumatism* 52:865-864, 2004) and rheumatoid arthritis synovial fibroblasts (Jungel et al., *Arthritis & Rheumatism* 50:1468-1476, 2004). Moreover, autoimmune, diabetic NOD mice have increased IL-21 receptor expression (King et al., *Cell* 117: 265-277, 2004.) It has been shown that IgG and IL-21 expression is increased in the BXSB-Yaa mouse model which develop an autoimmune lupus erythematosus-like disease (Ozaki et al., *J. Immunol.* 173:5361-5371, 2004); IL-21 expression is higher in lupus-prone Sanroque mice (Vinuesa et al. *Nature* 435:452, 2005); IL-21 expression is higher in patients with Crohn's disease (Monteleone, et al., *Gastroenterology* 128:687-694, 2005).

A therapeutically effective amount of an anti-IL-21 antibody refers to an amount of antibody which when administered to a subject is effective to prevent, delay, reduce or inhibit a symptom or biological activity associated with a disease or disorder. Administration may consist of a single dose or multiple doses and may be given in combination with other pharmaceutical compositions.

The present invention provides compositions and methods for using IL-21 antagonists in inflammatory and immune diseases or conditions such as pancreatitis, type I diabetes (IDDM), Graves Disease, inflammatory bowel disease (IBD), Crohn's Disease, ulcerative colitis, irritable bowel syndrome, multiple sclerosis, rheumatoid arthritis, diverticulosis, systemic lupus erythematosus, psoriasis, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, graft versous host disease, transplant rejection, atopic dermatitis, antiphospholipid syndrome, and asthma, and other autoimmune diseases.

Contact Dermatitis

Allergic contact dermatitis is defined as a T cell mediated immune reaction to an antigen that comes into contact with the skin. The CLA+ T cell population is believed to be involved in the initiation of dermatitis since allergen dependent T cell responses are largely confined to the CLA+ population of cells (See Santamaria-Babi, L. F., et al., *J Exp Med* 181:1935, (1995)). Recent data have found that only memory (CD45RO+) CD4+ CLA+ and not CD8+ T cells proliferate and produce both type-1 (IFN-γ) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol* 51:32, (2004).

In animal models, it has been demonstrated that allergic contact dermatitis is T cell-dependent and that the allergic-responsive T cells migrate to the site of allergen application. See generally: Engeman T. M., et al., *J Immunol* 164:5207, (2000); Ferguson T. A. & Kupper T. S. *J Immunol* 150:1172, (1993); and Gorbachev A. V. & Fairchild R. L. *Crit Rev Immunol* 21:451 (2001).

Atopic Dermatitis

Atopic dermatitis (AD) is a chronically relapsing inflammatory skin disease with a dramatically increasing incidence over the last decades. Clinically AD is characterized by highly pruritic, often excoriated, plaques and papules that show a chronic relapsing course. The diagnosis of AD is mostly based on major and minor clinical findings. See Hanifin J. M., *Arch Dermatol* 135:1551 (1999). Histopathology reveals spongiosis, hyperparakeratosis and focal parakeratosis in acute lesions, whereas marked epidermal hyperplasia with hyperparakeratosis and parakeratosis, acanthosis/hypergranulosis and perivascular infiltration of the dermis with lymphocytes and abundant mast cells are the hallmarks of chromic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol* 14:13, (2004)). A significant increase in circulating CLA+ T cells among AD patients compared with control individuals has been documented (See Teraki Y., et al., *Br J Dermatol* 143:373 (2000), while others have demonstrated that memory CLA+ T cells from AD patients preferentially respond to allergen extract compared to the CLA-population (See Santamaria-Babi, L. F., et al., *J Exp Med.* 181:1935, (1995)). In humans, the pathogenesis of atopic disorders of the skin have been associated with increases in CLA+ T cells that express increased levels of Th-2-type cytokines like IL-5 and IL-13. See Akdis M., et al., *Eur J Immunol* 30:3533 (2000); and Hamid Q., et al., *J Allergy Clin Immunol* 98: 225 (1996).

NC/Nga mice spontaneously develop AD-like lesions that parallel human AD in many aspects, including clinical course and signs, histopathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy* 58:139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest*, 101:1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002).

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of anti-IL-21 antibodies to these CIA model mice are used to evaluate the use of anti-IL-21 antibodies to ameliorate symptoms and alter the course of disease.

Inflammatory Bowel Disease (IBD)

In the United States approximately 500,000 people suffer from inflammatory bowel disease (IBD) which can affect either colon and rectum (ulcerative colitis) or both, small and large intestine (Crohn's Disease). The pathogenesis of these diseases is unclear, but they involve chronic inflammation of the affected tissues. Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of anti-IL-21 antibodies to these TNBS, DSS or CD4 transfer models can be used to evaluate the use of IL-21 antagonists to ameliorate symptoms and alter the course of gastrointestinal disease. IL-21 may play a role in the inflammatory response in colitis, and the neutralization of IL-21 activity by administrating IL-21 antagonists is a potential therapeutic approach for IBD.

Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. Anti-IL-21 antibodies of the present invention, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy. Anti-IL-21 antibodies can be tested using a recently developed a model of psoriasis based on the CD4+CD45RB transfer model (Davenport et al., *Internat. Immunopharmacol.*, 2:653-672, 2002).

In addition to other disease models described herein, the activity of anti-IL-21 antibodies on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in ther art may be used to evaluate IL-21 antagonists, such as human psoriatic skin grafts implanted into AGR129 mouse model, and challenged with an appropriate antagonist (e.g., see, Boyman, O. et al., *J. Exp. Med.* Online publication #20031482, 2004, incorporated hereing by reference). Similarly, tissues or cells derived from human colitis, IBD, arthritis, or other inflammatory lestions can be used in the SCID model to assess the anti-inflammatory properties of the anti-IL-21 antibodies described herein.

Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbio.l Immunol* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Cutan. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model.

Systemic Lupus Erythematosus

Systemic lupus erythematosus (SLE) is an immune-complex related disorder characterized by chronic IgG antibody production directed at ubiquitous self antigens (e.g. anti-dsDNA). The effects of SLE are systemic, rather than localized to a specific organ. Multiple chromosomal loci have been associated with the disease and may contribute towards different aspects of the disease, such as anti-dsDNA antibodies and glomerulonephritis. CD4+ T cells have been shown to play an active part in mouse models of SLE (Horwitz, *Lupus* 10:319-320, 2001; Yellin and Thienel, *Curr. Rheumatol. Rep.*, 2:24-37, 2000). The role for CD8+ T cells is not clearly defined, but there is evidence to suggest that "suppressor" CD8+ T cell function is impaired in lupus patients (Filaci et al., *J. Immunol.*, 166:6452-6457, 2001; Sakane et al, *J. Immunol.*, 137:3809-3813, 1986).

IL-21 has been shown to modulate antibody responses by directly acting on B cells. (Mehta et al., *J. Immunol,* 170: 4111-4118, 2003; Ozaki et al., *Science,* 298:1630-1634, 2002; Suto et al., *Blood,* 100:4565-4573, 2002). For example, Ozaki et al., (*J. Immunol.* 173:5361, 2004) demonstrated that in BXSB-Yaa mice, a model for SLE, there is an elevated serum IL-21 level. Moreover, because IL-21 enhances $CD8^+$ T cell activity, administration of anti-IL-21 antibodies would provide a more robust T cell suppressor function in lupus patients where that function is compromised.

Anti-IL-21 antibodies can be administered in combination with other agents already in use in autoimmunity including immune modulators such as IFNγ, NOVANTRONE®, ENBREL®, REMICADE®, LEUKINE® and IL-2. Establishing the optimal dose level and scheduling for anti-IL-21 antibodies is done by a variety of means, including study of the pharmacokinetics and pharmacodynamics of anti-IL-21 antibodies; determination of effective doses in animal models, and evaluation of the toxicity of anti-IL-21 antibodies. Direct pharmacokinetic measurements done in primates and clinical trials can then be used to predict theoretical doses in patients that achieve plasma anti-IL-21 antibody levels that are of sufficient magnitude and duration to achieve a biological response in patients.

The invention is further illustrated by the following non-limiting examples.

EXAMPLES

Example 1

Preparation of IL-21 Proteins

IL-21 protein was produced as described in U.S. Patent Application No. 2006-0134754 and WO 04/055168, incorporated in its entirety herein. Briefly, a IL-21 nucleotide sequence was optimized and inserted in an *E. coli* expression vector which was deposited as ATCC Accession No. PTA-4853. The expression vector was introduced into *E. coli* strain W3110 (ATCC Accession No. 27325).

Host cells were fermented by growing *E. coli* strains expressing IL-21 in a suitable medium in shake flask culture to in a suitable medium and may be supplemented with carbohydrates, such as fructose, glucose, galactose, lactose, and glycerol. Isopropyl thiogalactopyranoside (IPTG) is may be added to the culture to a concentration 0.1 to 2.0 mM.

Following fermentation the cells were harvested by centrifugation, re-suspended in homogenization buffer and homogenized. After the homogenate was collected, it was resuspended a guanidine containing solution and the supernatant containing solubilized IL-21 was decanted and retained. The concentration of the IL-21 in the solubilized fraction was determined by reversed phase HPLC. Once the inclusion bodies were solubilized and denatured in guanidine solution containing a reducing agent, the reduced IL-21 was then oxidized in a controlled renaturation step. This step involved dilution in a refold buffer containing arginine hydrochloride, salts, and an oxido-shuffling system.

Purification of IL-21 protein may include purification of the IL-21 using hydrophobic interaction chromatography. The IL-21 may be further purified by high performance cation exchange chromatography. The methods for purifying IL-21 can comprise concentrating and carrying out a buffer exchange of the protein. This step is designed to concentrate the high performance cation exchange column eluate and exchange it into formulation buffer. The final column eluate pool is concentrated to increase the concentration of IL-21. Further purification of IL-21 to remove the remaining impurities and contaminants may be desirable. For example, an anion exchange column can be used to reduce the endotoxin level.

Example 2

Preparation of IL-21 Receptor Proteins

The IL-21 receptor (also designated as zalpha11 or IL-21r) heterodimer protein can be produced as described in U.S. Patent Application No. 2002-0137677, incorporated in its entirety herein. Briefly, a vector expressing a secreted human hzalpha11/hIL2Rgamma heterodimer is constructed. In this construct, the extracellular domain of hzalpha11 is fused to the CH1 domain of IgG γ1. The CH1 domain is cloned into a mammalian expression vector. The CL1 domain of the human K light chain is cloned in a mammalian expression vector.

A construct having human zalpha11 fused to $CH_1$ is made, and the vector is sequenced to confirm that the fusion is correct. A separate construct having hIL2Rgamma fused to CL1 can be also constructed. The resulting vector is sequenced to confirm that the human IL-2Rgamma/CL1 fusion is correct.

The human zalpha11 (IL-21r) and human IL-2Rgamma receptor fusions are co-expressed. Each expression vector is co-transfected into mammalian host cells by methods known to those skilled in the art. The transfected cells are selected for 10 days in methotrexate (MTX) and G418 (Gibco/BRL) for 10 days. The resulting pool of transfectants is selected again in MTX and G418 for 10 days.

The resulting pool of doubly-selected cells is used to generate protein. Factories (Nunc, Denmark) of this pool are used to generate conditioned medium. This serum free, conditioned media is passed over a protein-A column and eluted in fractions. Fractions found to have the highest concentration are pooled and dialyzed (10 kD MW cutoff) against PBS. Finally the dialyzed material is submitted for amino acid analysis (AAA). The purified soluble human zalpha11 receptor/IL-2Rgamma receptor can be used to assess its ability to compete for binding of the human zalpha11 Ligand a BaF3 proliferation assay.

B. The extracellular domain of human zalpha11 fused to Fc9 (Fc region of human gamma1 (Kabat numbering 221-447; Kabat et al, Sequences of Proteins of Immunological Interest, U.S. Dept. Health and Human Serv., Bethesda, Md., 1991)) with an GluGlu tag (Grussenmeyer et al., Proc. Natl. Acad. Sci. USA 82:7952-4, 198)) at the carboxyl terminus was generated by overlap PCR. The cDNA was inserted into pZMP31 (described in US Patent application, US2003/023414; a hybrid vector having a cytomegalovirus enhancer and myeloproliferative sarcoma virus promoter) by recombination in yeast. The extracellular domain of the human IL2 receptor common gamma chain was fused to Fc9 with a 6×His tag at the carboxyl terminus of Fc9. This construct was inserted into pZMP21z by yeast recombination using the same method as described for zalpha11 Fc9CEE. The resulting constructs were sequenced to verify that the inserts were correct. Both plasmids were transfected into suspension, serum-free-adapted CHO cells by electroporation and selected in protein-free PFCHO media (BioWhittaker) without hypoxanthine and thymidine with 200 ng/mL zeomycin added. These cells were then selected in the same medium plus increasing concentrations of methotrexate until the cells were resistant to both 1 uM methotrexate and 200 ng/mL zeomycin. The cells were tested for production of heterodimeric IL21 receptor by western blot analysis for the presence of both EE and his tags.

The design of zcytor26f2 (extracellular domain of the human IL2 receptor common gamma chain was fused to Fc9 with a 6×His tag) is such that three tags are available for purification (GluGlu, His, and Fc), of which two are utilized to best discriminate heterodimer from the two homodimer contaminants. All molecules containing an Fc domain (homodimer contaminants and heterodimer target) were captured and purified from host cell components and related media products. The pool containing all species was concentrated and injected over an appropriate size exclusion column (Superdex 200) in order to remove aggregates. The SEC pool containing all three species (two homodimers and one heterodimer) was subjected to Immobilized Metal Affinity Chromatography (IMAC) using the Ni counter ion under highly discriminating load and elution conditions. The IMAC elution pool contained highly pure heterodimer, with only residual homodimer contamination. IMAC pool buffer was exchanged into formulation buffer using size exclusion chromatography (Superdex 200), which also removes any residual aggregation products. This IL-21 heterodimeric protein was used as a comparator when testing an antibody's neutralizing activity.

Example 3

Preparation of IL-21 Monoclonal Antibodies

Rat monoclonal antibodies are prepared by immunizing 4 female Sprague-Dawley Rats (Charles River Laboratories, Wilmington, Mass.), with the purified recombinant IL-21 protein. The rats are each given an initial intraperitoneal (IP) injection of 25 μg of the purified recombinant protein in Complete Freund's Adjuvant (Pierce, Rockford, Ill.) followed by booster IP injections of 10 μg of the purified recombinant protein in Incomplete Freund's Adjuvant every two weeks. Seven days after the administration of the second booster injection, the animals are bled and serum is collected.

The IL-21-specific rat sera samples are characterized by ELISA using 1 ug/ml of the purified recombinant IL-21 receptor protein as the specific antibody target. ELISAs comprise preparing IL-21 antigen, coating the wells of a 96-well microtiter plate with the antigen, adding the rat sera of interest to the wells and incubating for a period of time to allow the antibodies in the rat sera to bind to the antigen. A second detection antibody (which recognizes the antibodies of interest contained within the rate sera) conjugated to a detectable compound conjugated to a detectable compound such as an enzymatic substrate (e.g., horseradish peroxidase or alkaline phosphatase) is added to the wells. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Splenocytes are harvested from a single high-titer rat and fused to SP2/0 (mouse) myeloma cells using PEG 1500 in a single fusion procedure (4:1 fusion ratio, splenocytes to myeloma cells, "Antibodies: A Laboratory Manual", E. Harlow and D. Lane, Cold Spring Harbor Press). Following 9 days growth post-fusion, specific antibody-producing hybridoma pools are identified by ELISA using 500 ng/ml of the recombinant IL-21 protein as specific antibody target. Positive hybridoma pools are analyzed further for their ability to block the cell-proliferative activity ("neutralization assay") of purified recombinant IL-21 protein on BaF3 cells expressing the IL-21 receptor sequence.

Hybridoma pools yielding positive results by the "neutralization assay" are cloned at least two times by limiting dilution.

The monoclonal antibodies produced by clones are characterized in a number of ways including binning (i.e, determining if each antibody could inhibit the binding of any other binding), relative affinity, and neutralization. Monoclonal antibodies purified from tissue culture media are characterized for their ability to block the cell-proliferative activity ("neutralization assay") of purified recombinant IL-21 on Baf3 cells expressing the receptor sequences. "Neutralizing" monoclonal antibodies are identified in this manner.

Samples were taken from the hybridoma pools and assayed using both the neutralization assay and a direct titration ELISA. In this assay a sample was titrated out using four-fold serial dilutions to see which clone could maintain the highest OD reading. Using the results from both the neutralization and titration assays, specific clones from each initial master well were chosen to go forward with. Another neutralization screen was performed that ran all these samples in the same assay and at this point the number of cell lines was narrowed down to four top picks. These were subjected to an additional round of cloning to ensure culture homogeneity and screened using the direct ELISA. After one more titration assay, two final IL-21 clones were chosen and designated 268.5.1.11.42.1.4.3.9 (rat anti-mouse IL-21, ATCC Accession no. PTA-10394) and 272.21.1.3.4.2 (rat anti-human IL-21, ATCC Accession no. PTA-10395). The monoclonal antibodies produced by these hybridoma clones can be cultured in a growth medium of 90% Iscove's Modified Dulbecco's medium with 2 mM L-glutamine, 100 mg/mL penicillin, and 100 mg/mL streptomycin sulfate, and 10% Fetal Clone I Serum (Hyclone Laboratories). The clones can be propagated by starting cultures at $2 \times 10^5$ cells/ml and maintaining between $1 \times 10^5$ and $5 \times 10^5$ cell/ml at 37° C. and 5-6% CO. Cells can be adapted to serum free conditions upon subsequent transfers. Cells that are frozen are stored in 90% serum, 10% DMSO and stored in vapor phase of liquid nitrogen freezer.

Example 4

Serum Screening of Monoclonal Antibodies

The activity of anti-IL-21 antibodies is measured using a cell-based potency bioassay. The bioassay utilizes a BaF3 reporter cell line that was engineered to express the IL-21 receptor (IL-21R) through stable transfection with IL-21R cDNA. The IL-21R/BaF3 transfected cells are highly dependent upon rIL-21 or IL-3 for growth and, in their absence, are unable to proliferate and undergo apoptosis within 24 hours. In the cell-based bioassay, the IL-21R/BaF3 transfected cells are incubated with varying concentrations of serum containing anti-IL-21 antibodies and subsequent cellular proliferation is measured.

Example 5

Characterization of Antibodies

Epitope Binning

Epitope binning studies are performed on a Biacore1000™ system (Biacore, Uppsalla Sweden). Methods are programmed using Method Definition Language (MDL) and run using Biacore Control Software, v 1.2. Polyclonal goat anti-Mouse IgG Fc antibody (Jackson ImmunoResearch Laboratories, West Grove, Pa.) is covalently immobilized to a Biacore CM5 sensor chip and is used to bind (capture) the primary monoclonal antibody of test series to the chip. Unoccupied Fc binding sites on the chip are then blocked using a polyclonal IgG Fc fragment (Jackson ImmunoResearch Laboratories, West Grove, Pa.). Subsequently, IL-21 is injected and allowed to specifically bind to the captured primary monoclonal antibody. The Biacore instrument measures the mass of protein bound to the sensor chip surface, and thus, binding of both the primary antibody and IL-21 antigen are verified for each cycle. Following the binding of the primary antibody and antigen to the chip, a monoclonal antibody of the test series is injected as the secondary antibody, and allowed to bind to the pre-bound antigen. If the secondary monoclonal antibody is capable of binding the IL-21 antigen simultaneously with the primary monoclonal antibody, an increase in mass on the surface of the chip, or binding, is detected. If, however, the secondary monoclonal antibody is not capable of binding the IL-21 antigen simultaneously with the primary monoclonal antibody, no additional mass, or binding, is detected. Each monoclonal antibody tested against itself is used as the negative control to establish the level of the background (no-binding) signal. Data are compiled using BioEvaluation 3.2 RCI software, then loaded into Excel™ for data processing.

Western Blotting

The ability of the neutralizing monoclonal antibodies from clones to detect denatured and reduced/denatured IL-21 from two sources is assessed using a Western blot format. A rabbit polyclonal antibody known to detect IL-21 in a Western blot format is used as a positive control.

IL-21 protein is loaded onto 4-12% NuPAGE Bis-Tris gels (Invitrogen, Carlsbad, Calif.) in either non-reducing or reducing sample buffer (Invitrogen) along with molecular weight standards (SeeBlue; Invitrogen), and electrophoresis is performed. Following electrophoresis, protein is transferred from the gel, the nitrocellulose blots are blocked overnight and exposed to each antibody. The blots are then probed with a secondary antibody conjugated to horseradish peroxidase; sheep anti-mouse IgG-HRP (Amersham: Piscataway, N.J.) for the monoclonal antibodies and donkey anti-rabbit Ig-HRP (Amersham) for the polyclonal antibodies. Bound antibody is detected using a chemiluminescent reagent (Lumi-Light Plus Reagent: Roche, Mannheim, Germany) and images of the blots were recorded on a Lumi-Imager (Mannheim-Boehringer).

Example 6

DTH Mouse Model

DTH responses are classic immune responses that are initiated by CD4+ T cells and mediated by T cells, neutrophils and macrophages. A DTH response is a good indicator of a CD4+ T cell mediated response. Mice are immunized subcutaneously with chicken ovalbumin protein (OVA) in either of 2 adjuvants, RIBI or CFA. This phase is called the sensitization phase (days 0-6). Ear measurements are taken seven days later. Mice are then injected in the ear with control PBS (left ear) or OVA (right ear). This phase is called the challenge phase (days 7-8) Immune responses generated to OVA induce inflammation in the ear resulting an increase in ear thickness in 24 hours in the OVA-treated, but not in the PBS-treated ear. This is measured using calipers.

C57BL/6 mice (n=8/group) are immunized in the back with 100 μg chicken ovalbumin (OVA) emulsified in RIBI adjuvant (Corixa, Seattle, Wash.) in a total volume of 200 μl. A 0.5 mg/ml of ovalbumin is added to a single vial of RIBI and vortexed vigorously for 2 minutes to form an emulsion that is used to inject mice. Seven days after the immunization, mice are injected with 10 μL1 PBS in the left ear (control) and with 10 μg OVA in PBS in the right ear in a volume of 10 μl. Ear thickness of all mice is measured before injecting mice in the ear (0 measurement). Ear thickness is measured 24 hours after challenge. The difference in ear thickness between the 0 measurement and the 24 hour measurement is calculated and is reflective of the inflammation in the ear. Groups of mice are injected with PBS or different concentration of anti-IL-21 antibody intra-peritoneally from either days 0-6 (sensitization phase) or from days 7-8 (challenge phase). The injection on day 7 and 8 is given 2 hours before measuring ear thickness at the 0 and 24 hour time points. At the end of the 24 hour period, once ear thickness was measured, the ears were cut and placed in formalin for histological analysis.

Example 7

Mouse Model for Multiple Sclerosis

To test if anti-IL-21 has any effects on multiple sclerosis, the ability of anti-IL-21 antibodies to inhibit experimental autoimmune encephalomyelitis (EAE), a mouse model for MS is tested. The well characterized myelin oligodendrocyte glycoprotein (MOG) 35-55 peptide immunization model in C57BL/6 mice is used. The experiment is run to determine that anti-IL-21 antibody could delay and/or inhibit disease scores in EAE either by inhibiting DC mediated antigen presentation or by enhancing CD8 T cell responses. Absence of efficient CD8 T cell responses in this model exacerbates EAE (Malipiero et. al., *Eur. J. Immunol*, 27:3151-3160, 1997). Delayed onset of disease in the EAE model in a dose dependent manner suggests that use of anti-IL-21 antibody may be beneficial in MS.

Experimental autoimmune encephalomyelitis (EAE) is a mouse model for MS. In one such model, C57BL/6 mice are immunized with 100 μg MOG pepetide (MOG35-55) or 100 μg recombinant MOG protein emulsified in RIBI adjuvant. Two milliliters of a 0.5 mg/ml preparation of the MOG35-55 in PBS is added to a vial of RIBI and vortexed vigorously to emulsify the solution or a 1:1 ratio of recombinant MOG in DFA is prepared. The backs of mice are shaved and 100 μg MOG/RIBI is injected s.c in the backs of mice. Weights of mice are taken 2 days before and every day after the immunization. Mice are then injected on day 2 i.v. with 200 μL1 pertussis toxin (PT), a final concentration of 200 ng/mouse. Mice are monitored daily for clinical scores. Groups of mice are injected i.p. with 200 μL1 PBS, 100 μg BSA, 10 μg-200 μg anti-IL-21 antibody in a 200 μl volume from days 0-20, or 3× a week for 3 weeks. The weights of mice, clinical scores and incidence are evaluated and plotted for analysis.

Example 8

CD4+CD45RBhi (CD25−) Colitis and Psoriasis Mouse Model

Transfer of CD4+ CD45RBhi or CD4+CD25− T cells into syngenic SCID mice results in colitis in the mice. Co-transfer of regulatory T cells (CD4+CD25+ or CD4+CD45RBlo) inhibits this colitis. After transfer of CD4+CD25− T cells into mice, if mice are additionally injected with staphylococcal enterotoxin B (SEB), mice not only develop colitis, but also psoriasis. Anti-IL-21 antibody is administered from days 0-21 after cell transfer and symptoms for colitis and psoriasis are monitored. Inhibiton of psoriatic score or colitis (histology) indicates that anti-IL-21 antibody can inhibit these autoimmune diseases.

Spleens and inguinal lymph nodes are isolated from B10.D2 mice. Single cell suspensions are formed and counted. Using the Miltenyi Bead system, CD25+ cells are sorted out by positive selection. Cells are stained with CD25−PE (BD Pharmingen) at 1:100 dilution and incubated for 15 minutes. Excess antibody is washed out and the cells are incubated with 10 ul anti-PE beads/106 cells for 20 minutes. The cells are washed with PBS and passed over an LS column (Miltenyi Biotech). Cells that pass through the column (CD25) are retained for further analysis. A CD4 enrichment cocktail (Stem Cell technologies) is added (1:100) to these CD25− cells and incubated for 15 minutes. Cells are washed with PBS. A 1:10 dilution of anti-biotin tetramer is added to the cells for 15 minutes followed by a magnetic colloid (60 ul/106 cells) for 15 minutes (all from Stem Cell Technologies). Cells are passed through a negative selection column (0.5", Stem cell Technologies). Cells that pass through are the CD4+CD25− cells. Purity is analyzed using flow cytometry. $0.4 \times 10^6$ cells are injected i.v into naïve CB-17 SCID mice in a total volume of 200 μl. Mice are injected i.p with 10 μg SEB the following day (d1). Symptoms for psoriasis and colitis are followed from 2-5 weeks. Groups of mice are injected i.p. with PBS, 100 μg BSA or 10-200 μg IL-21 from days 1-20, or 3× a week for 3 weeks.

Inhibiton of psoriatic and colitis symptoms in anti-IL-21 antibody treated mice indicates that anti-IL-21 antibodies can inhbit autoimmune symptoms in this model for psoriasis and colitis.

Example 9

Contact Hypersensitivity Mouse Model

Contact hypersensitivity can be induced in mice using a variety of contact allergens including dinitrofluorobenzene (DNFB) and oxazolone. Mice are sensitized topically with the allergen in a vehicle of acetone and olive oil and then challenged in the ear with the allergen in olive oil alone. Change in ear thickness is a measure of the immune response against the allergen. Anti-IL-21 antobodies are administered either at the sensitization phase (d0-5) or during the challenge phase (d5-6). Inhibition of ear thickness by IL-21 indicates a role for IL-21 in inhibiting contact hypersensitivity.

C57Bl/6 mice are painted in the back with 0.5% DNFB in acetone:olive oil (4:1) or acetone:olive oil alone on d0. On d5, ear thickness of mice is measured using calipers and mice are challenged in the ears with olive oil alone (control) or 0.25% DNFB in olive oil by dropping a 25 μl solution onto the ear. Change in ear thickness is measured on d6 and the inflammation calculated as a difference in ear thickness between d5 and d6. Groups of mice are injected i.p. with PBS or 10-100 μg anti-IL-21 antibodies on either days 0-5 or days 5-6.

Inhibition of ear thickness by anti-IL-21 antibodies demonstrate that anti-IL-21 antibodies can be useful in inhibiting contact hypersensitivity.

Splenocytes are harvested and pooled from two high-titer Balb/c mice and fused to P3-X63-Ag8.653 mouse myeloma cells using PEG 1450 in a single fusion procedure (2:1 fusion ratio, splenocytes to myeloma cells, "Antibodies: A Laboratory Manual", E. Harlow and D. Lane, Cold Spring Harbor Press). Following 9 days growth post-fusion, specific antibody-producing hybridoma pools are identified by Direct and Capture ELISA using recombinant IL-21 protein, untagged and human IgG Fc tagged, as specific antibody target. Positive hybridoma pools are analyzed further for their ability to block the cell-proliferative activity ("neutralization assay") of purified recombinant IL-21 protein on BaF3 cells expressing the IL-21 receptor sequence. Monoclonal antibodies purified from tissue culture media are characterized for their ability to block the cell-proliferative activity ("neutralization assay") of purified recombinant IL-21 on Baf3 cells expressing the receptor sequences. "Neutralizing" monoclonal antibodies are identified in this manner.

Hybridoma pools yielding positive results by the "neutralization assay" and ELISA formats are cloned at least two times by limiting dilution. In these assays, samples are titrated using four-fold serial dilutions to see which clone will maintain the highest OD reading Using the results from both the neutralization and titration assays, two specific clones from each initial master well are selected for further analysis. These are subjected to an additional round of cloning to ensure culture homogeneity and screened using the Direct ELISA. After one additional titration assay, two final IL-21 clones are selected. Hybridoma clones are cultured in a growth medium of 90% Iscove's Modified Dulbecco's medium with 2 mM L-glutamine, 100 mg/mL penicillin, and 100 mg/mL streptomycin sulfate, and 10% Fetal Clone I Serum (Hyclone Laboratories). The clones are propagated by seeding cultures at $2\times10^5$ cells/ml and maintaining between $1\times10^5$ and $5\times10^5$ cell/ml at 37° C. and 5-6% CO. Cells are adapted to serum free conditions upon subsequent transfers. Cells are frozen in 90% serum, 10% DMSO and stored in vapor phase of a liquid nitrogen freezer.

The purified monoclonal antibodies produced by the hybridoma clones are characterized in a number of ways including binning (i.e, determining if each antibody could inhibit the binding of any other binding), epitope mapping using peptides, relative affinity, and neutralization.

Example 11

Selection of Peptide Sequences for Use in the Evaluation of Monoclonal Antibodies Directed Against Human IL-21

An assessment of the binding of murine anti-human IL21 antibodies to the various domains of IL-21 was conducted in part through the ability of the monoclonal antibodies to bind synthetic peptides derived from the native human IL-21 sequence. Peptides of 18-29 amino acids were selected to provide significant coverage of the cytokine polypeptide while focusing on domains predicted from cytokine mutein studies and the structure of IL-21 related cytokines to be important in receptor binding or activation. Peptides in this size range are also efficient to manufacture and are of a size that may provide limited secondary structure for antibody recognition. Peptides 1, 3, and 4 were synthesized with an amidated carboxyl terminus to better mimic the electrostatic charge found in the native peptide bonds.

Peptide #1

The N-terminus of human IL-21 following the mammalian processing of the signal peptide sequence, along with the adjacent amino acid sequence of IL-21 (SEQ ID NO: 6) was chosen for one peptide. Mammalian expression of human IL-21 and N-terminal sequencing of the cytokine had previously demonstrated that following cleavage of the signal peptide, the resulting N-terminal amino acid was the pyroglutamate derivative of glutamine-30. This derivative was chosen for the N-terminal amino acid for the peptide and along with the subsequent 20 amino acids found at the amino terminus of human IL-21. To permit efficient and specific coupling of the peptide to carrier proteins or solid phase matrix necessary for the analysis with this peptide, an additional cysteine residue was added to the carboxyl terminus of the peptide. The complete peptide sequence is pyroGQDRHMIRMRQLIDIVDQLKCamide (SEQ ID NO: 1).

Peptide #2

The second peptide was chosen due to its hydrophilic character, the presence of proline residues (predicted non-helical segment), and its location in the IL-21 sequence between the predicted A- and B-helical regions. The carboxy terminal end of the peptide was selected due to the presence of a cysteine residue in the human IL-21 polypeptide sequence. The peptide sequence is NDLVPEFLPAPEDVETNC (SEQ ID NO: 2).

Peptide #3

This peptide sequence was selected for its predicted location comprising a significant portion of the hydrophilic C-helix of the IL-21 structure. This very hydrophilic region is predicted to be important in ligand-receptor interaction, and the peptide span was also selected to allow for the inclusion of a native cysteine residue (Cys-122) to enable efficient conjugations when appropriate as noted above. The peptide sequence is NVSIKKLKRKPPSTNAGRRQKHRLTCamide (SEQ ID NO: 3).

Peptide #4

This peptide was selected due to its location near the carboxyl terminus of the cytokine and because studies utilizing IL-21 muteins have demonstrated this peptide region to be important for ligand-receptor activation but not ligand binding. Mutation of Gln-145 and/or Ile-148 contained within the sequence of this peptide, have been shown to affect human IL-21 receptor activation. The 29 amino acid peptide was initiated at the native Cys-125 to enable its use in chemical coupling of the peptide as noted above, and to end at Ser-153. This serine is the final amino acid in murine IL-21 so the peptide sequence amino terminal of this residue is predicted to contain the elements of the human IL-21 sequence that are important for ligand activity. The peptide sequence is CDSYEKKPPKEFLERFKSLLQKMIHQHLSamide (SEQ ID NO: 4).

Example 12

Phosphorylated-STAT3 Assay for Detection of IL-21 Neutralization

Previously derived Baf3/human IL21 receptor (hIL-21R) transfectants were used (see, U.S. Pat. Nos. 6,307,024 and 6,686,178, incorporated herein by reference). The cells were washed three times in Baf3 bioassay media which consists of: RPMI, 1× Glutamax, 10% Fetal Bovine Serum, 50 uM Beta-mercaptoethanol, 200 ug/mL Zeocin, 1 mg/mL G418 (all from Invitrogen Corporation, Carlsbad, Calif.). After third wash, cells were counted using standard methods (hemacytometer) and resuspended to $6\times10^5$ cells per mL in bioassay media. Cells were then plated in a 96-well round bottom tissue culture plate at 30,000 cells per well. The plate was then transferred to a 37° C. tissue culture incubator while the other assay plates were set up.

The samples plate was then set up with 30 uL of 2.0 ng/mL human IL-21 plus 30 uL of one of the following: diluted mouse serum (1:10, 1:50 or 1:100 final concentrations), media, anti-IL-21 neutralizing antibody (various lots and concentrations), soluble hIL-21R (example 2) or irrelevant controls. The plate was then transferred to a 37° C. incubator. After 30-40 minutes, both the cell plate and the sample plates were removed from the incubator and 50 uL of each well in the sample plate was transferred to the cell plate and mixed. The plates were then placed back in the 37° C. incubator for exactly 8 minutes. At this point, the reaction was stopped by placing the plate on ice and adding 150 uL of ice cold BioPlex Cell Wash Buffer (BioRad Laboratories, Hercules, Calif.). The plate was centrifuged for 5 minutes at 1500 RPM and 4° C. Following centrifugation, the supernatant was discarded into the sink and cells were lysed in 60 uL BioPlex Cell Lysis Buffer containing Factor 1, Factor 2 and PMSF (all from BioRad). Lysed cells were pipetted to break up clumps and then shaken at 600 RPM on at 4° C. for 20 minutes. The plate was then centrifuged again for 20 minutes at 3000 RPM at 4° C. After centrifugation, 55 uL of lysate was removed and mixed with 55 uL of Phosphoprotein Testing Assay Buffer (BioRad).

At this point a filter plate was pre-wetted with 50 uL Phosphoprotein Wash Buffer (PWB), aspirated and 50 uL of PhosphoSTAT3 Coupled Beads (BioRad) plated. These beads were then aspirated and the plate was washed three times with 75 uL of PWB. Following final aspiration, 50 uL of diluted lysate was transferred to the plate which was then covered and shaken overnight at room temperature. The following morning, the plate was washed three times with PWB, and biotinylated-PhosphoSTAT3 Detection Antibodies (BioRad) were then added for 20 minutes at room temperature. The plate was washed three more times in PWB and then Streptavidin-PE was added for 10 minutes. Finally, the plate was washed three times with Phosphoprotein Resuspension Buffer (PRB) and the beads were resuspended in 125 uL of PRB.

Total phosphorylated-STAT3 was measured in each well by following the standard Luminex 100 data collection protocol as recommended by the manufacturer (Luminex Inc., Austin, Tex.). Data were then analyzed and expressed as fold-induction of phosphorylated-STAT3 as compared to media alone.

Serum from mice immunized with various IL-21 peptides (see table 1) was tested for neutralization of IL21-induced STAT3 phosphorylation. IL-21 was premixed with a dilution of serum for 30 minutes at 37° C. This solution was then added to Baf3/hIL21R transfectants for 8 minutes. The reaction was then stopped, cells lysed and phosphorylated-STAT3 measured. The fold increase in phosphoylated-STAT3 is calculated using the "media alone" control as a baseline. Lower numbers correlate to stronger IL-21 neutralization. The data is summarized in Table 2 below.

Briefly: one of three mice (#1976) immunized with peptide #1 and two of three mice (#1979, 1980) immunized with peptide #2, generated IL-21 neutralizing antibodies. No mice immunized with peptides #3 and #4 generated neutralizing antibodies. The neutralization seen in the 1:10 dilution column may be due to a serum effect, not specific anti-IL-21 activity (refer to "irrelevant serum" data).

TABLE 1

IL21 peptides and corresponding serum sample numbers

| Sample # | Peptide # |
|---|---|
| 1976-1978 | Peptide #1 (see example 11) |
| 1979-1981 | Peptide #2 (see example 11) |
| 1982-1984 | Peptide #4 (see example 11) |
| 1985-1987 | Peptide #3 (see example 11) |
| 1988-1990 | Peptide #3 (see example 11) |

TABLE 2

Average fold increase in phosphorylated-STAT3 levels as compared to media

| | Serum Dilution | | |
|---|---|---|---|
| Sample# | 1:10 | 1:50 | 1:100 |
| 1976 | 1.89 | 5.07 | 5.15 |
| 1977 | 4.98 | 10.14 | 8.63 |
| 1978 | 6.72 | 8.33 | 12.99 |
| 1979 | 1.04 | 1.81 | 2.17 |
| 1980 | 0.65 | 1.4 | 1.81 |
| 1981 | 6.91 | 9.8 | 17.06 |
| 1982 | 4.04 | 10.8 | 12.73 |
| 1983 | 9.68 | 12.05 | 12.42 |
| 1984 | 5.84 | 10.84 | 11.78 |
| 1985 | 6.94 | 12.64 | 11.5 |
| 1986 | 9.01 | 13.41 | 16.61 |
| 1987 | 8.48 | 14.11 | 17.36 |
| 1988 | 4.56 | 8.66 | 9.38 |
| 1989 | 4.88 | 11.63 | 12.66 |
| 1990 | 9.56 | 10.29 | 14.58 |
| Controls | | | |
| Media Alone | 1 | | |
| IL-21 | 12.4 | | |
| NMS | 11.28 | 11.72 | 10.31 |
| Irrelevant Serum | 3.52 | 11.09 | 9.49 |

Example 13

Assay Description of Direct EIA

The ability of human IL-21 peptides (example 11) to bind anti-human IL-21 antibodies was assessed using a "direct" style ELISA assay. In this assay, wells of 96 well polystyrene ELISA plates were first coated with 100 µL/well of human IL-21 protein at a concentration of 1 µg/mL in Coating Buffer (0.1M $Na_2CO_3$, pH 9.6). Plates were incubated overnight at 4° C. after which unbound peptides were aspirated and the plates washed twice with 300 µL/well of Wash Buffer (PBS-Tween defined as 0.137M NaCl, 0.0022M KCl, 0.0067M $Na_2HPO_4$, 0.0020M $KH_2PO_4$, 0.05% v/w polysorbate 20, pH 7.2). Wells were blocked with 200 µL/well of Blocking Buffer (PBS-Tween plus 1% w/v bovine serum albumin (BSA)) for 1 hour, after which the plates were washed twice with Wash Buffer. Antibody dilutions were prepared in 5% FBS/IMDM medium and adjusted to 1 ug/ml. Duplicate samples of each antibody dilution were then transferred to the assay plates, 100 µL/well, in order to bind anti-human IL-21 peptides. Following 1 hour incubation at RT, the wells were aspirated and the plates washed twice as described above. Horseradish peroxidase labeled Goat anti Mouse IgG, Fc specific (Jackson ImmunoResearch Laboratories, West Grove, Pa.) at a dilution of 1:5000 with 5%/IMDM medium was then added to each well, 100 µL/well, and the plates incubated at RT for 1 hour. After removal of unbound HRP conjugated antibody, the plates were washed five times, 100 µL/well of tetra methyl benzidine (TMB) (BioFX Laboratories, Owings Mills, Md.) added to each well and the plates incubated for 3 minutes at RT. Color development was stopped by the addition of 100 µL/well of 450 nm TMB Stop Reagent (BioFX Laboratories, Owings Mills, Md.) and the absorbance values of the wells read on a Molecular Devices Spectra MAX 340 instrument at 450 nm.

Example 14

Characterization of Neutralizing Antibodies

Characterization of samples derived from hybridoma culture supernatant included binding assays using a human IL-21 Fc fusion protein, mouse IL-21 Fc fusion protein, a human IL-21 protein mutated at Gln 145 and Ile148 (SEQ ID NO: 6) and peptides described above. IL-21 Fc fusions are disclosed in U.S. Pat. Nos. 6,307,024 and 6,686,178, and methods for generating Fc fusions are disclosed in U.S. Pat. Nos. 5,155,027 and 5,567,584, all incorporated herein by reference. The IL-21 mutant protein is described in U.S. Pat. No. 6,929,932 and U.S. Patent Application No. 2005-0244930, all incorporated herein by reference.

TABLE 3

| Designation | Isotype | Neutralization | Binds hIL-21-Fc protein | Binds hIL-21 mutein | Binds mIL-21-mFc protein | Binds peptide number |
|---|---|---|---|---|---|---|
| Mouse Ab 338.17 | IgG1 | Yes | Yes | Yes | Yes | No. 3 |
| Mouse Ab 338.24 | IgG1 | Yes | Yes | Yes | Yes | No. 3 |
| Mouse Ab 338.25 | IgG1 | Yes | Yes | No | Yes | None |
| Mouse Ab 338.29 | IgG1 | Yes | Yes | Yes | Yes | No. 1 |
| Rat Ab 272.21.1.3.4.2 | IgG2a | Yes | No | Yes | Yes | No. 1 |

Mouse Ab 338.17 This sample bound the human IL-21 protein structure in an area predicted to be in the region of the C-Helix based on its ability to bind Peptide #3.

Mouse Ab 338.24 This sample bound the human IL-21 protein structure in an area predicted to be in the region of the C-Helix-C based on its ability to bind Peptide #3.

Mouse Ab 338.25 This sample bound the D-helix side of the molecule near Q145 and/or I148 (SEQ ID NO: 6) based on its ability to bind the native hIL-21 but not the hIL-21 mutein. The binding is likely to be to a discontinuous epitope based on its inability to bind peptide #4, which contains the native peptide sequence mutated in the IL-21 mutein, or the epitope may require the presence of Ser154-Ser162 of the human IL-21 sequence (SEQ ID NO: 6).

Mouse Ab 338.29 This sample bound the human IL-21 protein structure in an area predicted to be in the region of the A-Helix based on its ability to bind Peptide #1. Based on its ability to react moderately with a C-terminally conjugated Peptide #1 but react very strongly to the non-conjugated peptide, one would predict the epitope for this antibody to include the middle or C-terminal domain of Helix A as represented in Peptide #1.

Rat Ab 272.21.1.3.4.2 Based on its ability to react weakly with both the C-terminally conjugated and non-conjugated Peptide #1, its ability to neutralize hIL-21 but its inability to capture hIL-21-Fc from solution., this antibody binds to a largely discontinuous epitope on the human IL-21 protein structure comprising an area predicted to be in the region of the N-terminus of IL-21 and the A-Helix and require space near the adjacent C-terminus of hIL-21 where it is linked to the Fc fusion protein.

What is claimed is:

1. An isolated antibody that is capable of binding to the same epitope as a monoclonal antibody produced by the hybridoma designated ATCC Accession No. PTA-10395 for binding a human interleukin (IL)-21 antigen.

2. The isolated antibody of claim 1, wherein the antibody neutralizes the protein activity of human IL-21.

3. The antibody of claim 1, wherein said antibody is humanized.

4. An isolated antibody that is capable of binding to the same epitope as a monoclonal antibody produced by the hybridoma designated ATCC Accession No. PTA-10394 for binding a murine interleukin (IL)-21 antigen.

5. The isolated antibody of claim 4, wherein the antibody neutralizes the protein activity of human IL-21.

6. The antibody of claim 4, wherein said antibody is humanized.

* * * * *

UNITED STATES PATENT AND TRADEMARK OFFICE
CERTIFICATE OF CORRECTION

PATENT NO.      : 8,222,374 B2                          Page 1 of 1
APPLICATION NO. : 13/037585
DATED           : July 17, 2012
INVENTOR(S)     : Pallavur V. Sivakumar et al.

It is certified that error appears in the above-identified patent and that said Letters Patent is hereby corrected as shown below:

On the Title page, item (57) in the Abstract, at Col. 2, line 16:

Remove "graft versous host disease,".

Signed and Sealed this
Twenty-third Day of October, 2012

David J. Kappos
*Director of the United States Patent and Trademark Office*